US005798442A

United States Patent [19]
Gallant et al.

[11] Patent Number: 5,798,442
[45] Date of Patent: Aug. 25, 1998

[54] PEPTIDYL DERIVATIVES AS INHIBITORS OF PRO-APOPTOTIC CYSTEINE PROTEINASES

[75] Inventors: Michel Gallant, Montréal; Marc Labelle, Ville d'Ile Perrot; Yves Gareau, Ile Perrot; Donald W. Nicholson, Montreal, all of Canada

[73] Assignee: Merck Frosst Canada, Inc., Kirkland, Canada

[21] Appl. No.: 426,547

[22] Filed: Apr. 21, 1995

[51] Int. Cl.$^6$ .................................................. A61K 38/07
[52] U.S. Cl. ............................ 530/330; 530/331; 514/18
[58] Field of Search ............................ 514/18; 530/330, 530/331

[56] References Cited

U.S. PATENT DOCUMENTS

| | | | |
|---|---|---|---|
| 4,481,192 | 11/1984 | Cazaubon et al. | 424/177 |
| 4,582,821 | 4/1986 | Kettner et al. | 514/18 |
| 5,055,451 | 10/1991 | Krantz et al. | 514/19 |
| 5,278,061 | 1/1994 | Bull et al. | 435/212 |

FOREIGN PATENT DOCUMENTS

| | | |
|---|---|---|
| 0 263 202 | 4/1988 | European Pat. Off. . |
| 0 519 748 A2 | 12/1992 | European Pat. Off. . |
| 0 618 223 A2 | 10/1994 | European Pat. Off. . |
| WO 91/15577 | 10/1991 | WIPO . |
| WO93/09135 | 5/1993 | WIPO . |
| WO 93/16710 | 9/1993 | WIPO . |
| WO 94/06906 | 3/1994 | WIPO . |

OTHER PUBLICATIONS

Merck Veterinary Manual Seventh Ed., pp. 1019–1025 (1991) Diseases of Rats and Mice.
Howard, et al., Jour. Immun., vol. 147, pp. 2964–2969 (Nov. 1991).
Sleath, et al., J. Biol. Chem., vol. 265, pp. 14526–14528 (1990).
Thornberry, et al., Nature, vol. 356, pp. 768–774 (Apr. 30, 1992).
Patent Abstract of Japan, vol. 13(227) (C–600) (3575) (May 25, 1989) (JP 13 8 050).
Kostura, et al., Proc. Natl. Acad. Sci., vol. 86, pp. 5227–5231 (1989).
Black, et al., J. Biol. Chem., vol. 263, pp. 9437–9442 (1988).
Black, et al., J. Biol. Chem., vol. 264, pp. 5323–5326 (1988).
Black, et al., Feb Lett., vol. 247, pp. 386–390 (1989).
Jacobson, et al., Journal of Cell Biology, vol. 133, No. 5, Jun. 1996, pp. 1041–1051 "Role of Ced–3/ICE–Family Proteases in Staurosporine–induced Programmed Cell Death".
Zhu, et al., FEBS Letters, vol. 374, No. 2 (1995) pp. 303–308, "An ICE–like protease is a common mediator of apoptosis induced by diverse stimuli in human monocytic THP.1 cells".
Thornberry, et al., Protein Science, vol. 4, No. 1, pp. 3–12 (1995) "Interleukin–1Beta converting enzyme: A novel cysteine protease required for IL–1Beta production . . . ".

*Primary Examiner*—Cecilia J. Tsang
*Assistant Examiner*—David Lukton
*Attorney, Agent, or Firm*—Richard C. Billups; Curtis C. Panzer; David L. Rose

[57] ABSTRACT

Compounds having the formula I:

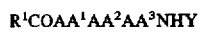

$$R^1COAA^1AA^2AA^3NHY$$

are inhibitors of apopain, an enzyme involved in the process of apoptosis. These compounds are useful as research tools as well as in the treatment of any condition in which reduced apoptosis would be beneficial, including immune deficiency syndromes (including AIDS), type I diabetes, pathogenic infections, cardiovascular and neurological injury, alopecia, aging, Parkinson's disease and Alzheimer's disease.

3 Claims, 13 Drawing Sheets

```
  1 MENTENSVDS KSIKNLEPKI IHGSESMDSG ISLDNSYKMD YPEMGLCIII
 51 NNKNFHKSTG MTSRSGTDVD AANLRETFRN LKYEVRNKND LTREEIVELM
101 RDVSKEDHSK RSSFVCVLLS HGEEGIIFGT NGPVDLKKIT NFFRGDRCRS
151 LTGKPKLFII QACRGTELDC GIETDSGVDD DMACHKIPVE ADFLYAYSTA
201 PGYSWRNSK DGSWFIQSLC AMLKQYADKL EFMHILTRVN RKVATEFESF
251 SFDATFHAKK QIPCIVSMLT KELYFYH
```

```
hICE_rel-III  .PARNG..MSHGIL..IVQACRGEKHGELW-VRDSP..HNVSWRDRTRGSIF..QAKAQMP.
hICE_rel-II   .PPRNG..MSHGIL..IVQACRGANRGELW-VRDSP..HNVSWRDSTMGSIF..RAKAQMP.
hICE          .PRRIG..MSHGIR..IIQACRGDSPGVVW-FKDSV..DNVSWRHPTMGSVF..DGRAQMP.
hICH-1        .EFRSG..LSHGVE..FIQACRGDETDRGVDQQDGK..GTAAMRNTKRGSWY..APGTEFH.
hCPP32        .TSRSG..LSHGEE..IIQACRGTELDCGIET-DSG..GYYSWRNSKDGSWF..SFDATFH.
ceCED-3       .PTRNG..LSHGEE..FVQACRGERRDNGFPVLDSV..QYVSWRNSARGSWF..QGSNILK.
               ○       ●●      ○●                  △  △○△△        △△
              179     237     283 285              333 341 347    383 385
                                      D/X
```

FIG. 4f

| ENZYME SOURCE | $K_m$ (μM) | $k_{on}$ (M$^{-1}$s$^{-1}$) | Ac-DEVD-CHO $K_i$ (nM) |
|---|---|---|---|
| THP-1 Cells | 9.7 ± 1.0 | 1.3 ± 0.2 × 10$^5$ | < 1 |
| Osteosarcoma Cells | 10.0 ± 1.1 | 1.0 ± 0.1 × 10$^5$ | < 1 |
| Chicken S/M Extracts | 13.6 ± 0.2 | 1.8 ± 0.1 × 10$^5$ | < 1 |

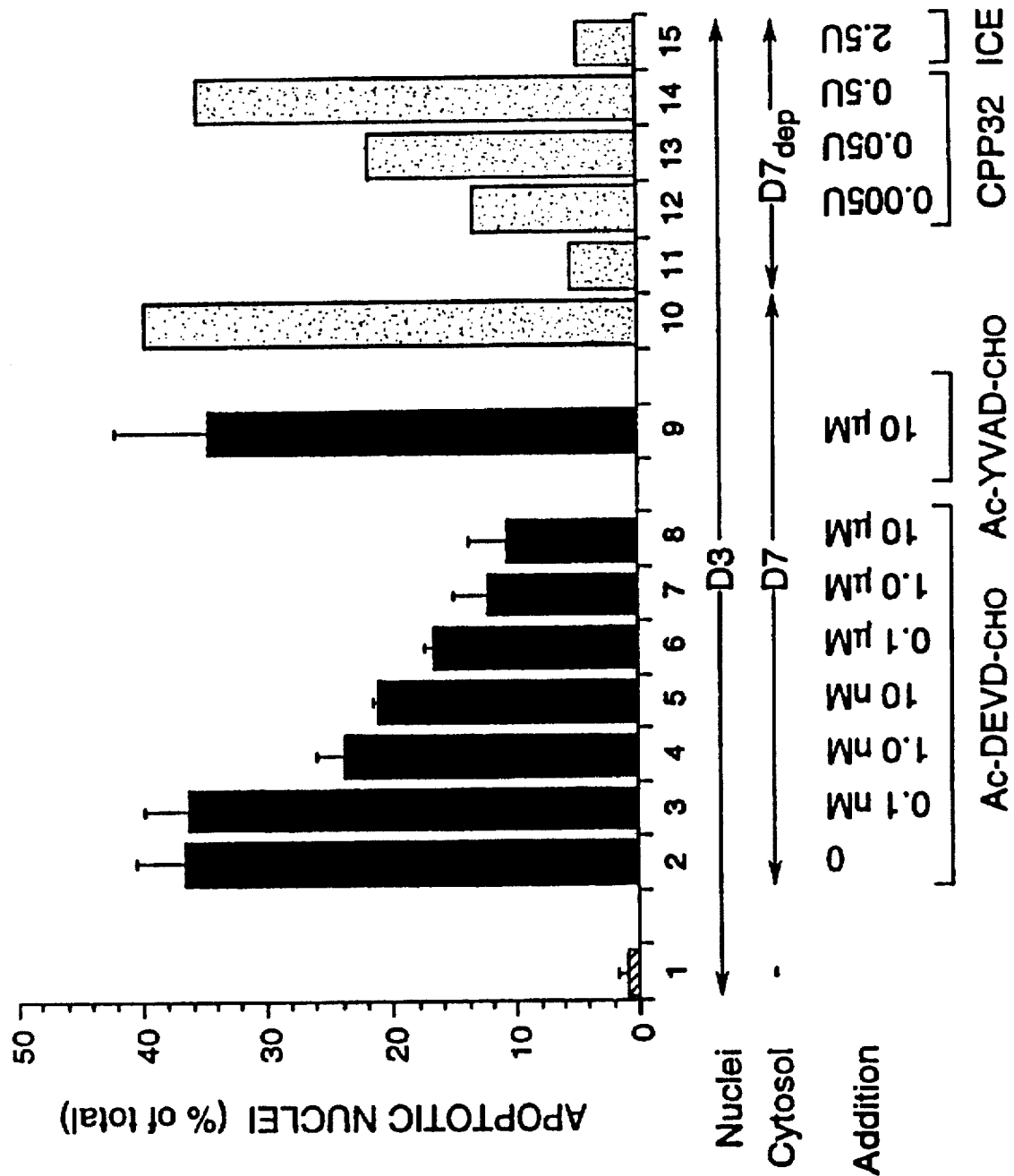

PEPTIDYL DERIVATIVES AS INHIBITORS OF PRO-APOPTOTIC CYSTEINE PROTEINASES

BACKGROUND OF THE INVENTION

In one aspect, this invention is directed to pro-apoptotic cysteine proteinases, such as apopain, the DNA encoding for same or its anti-sense, and an assay for identifying agents that modulate these proteinases.

In a second aspect this invention is directed to peptidyl derivatives which are modulators of the activity of pro-apoptotic cysteine proteinases, such as apopain, and their use in therapy and in identifying agents useful in the treatment of pro-apoptotic cysteine proteinase-mediated diseases.

Apoptosis constitutes a systematic means of cell suicide within an organism during normal morphogenesis, tissue remodelling as well as in response to pathogenic infections or other irreparable cell damage. Inappropriate apoptosis may underlie the aetiology of human diseases such as Alzheimer's, Parkinson's and Huntington's diseases, immune deficiency and autoimmune disorders, ischemic cardiovascular and neurological injury, alopecia, leukemias, lymphomas and other cancers, which therefore makes the control of apoptosis an important potential target for therapeutic intervention[1-4].

Several of the biochemical events that contribute to apoptotic cell death have recently been elucidated. Genetic evidence in nematodes, for example, has identified both positive and negative regulators of apoptosis[5]. The key pro-apoptotic gene, ced-3, encodes a putative cysteine protease which is related to mammalian interleukin-1β converting enzyme (ICE)[6], the first identified member of a new family of cysteine proteases with the distinguishing feature of a near absolute specificity for aspartic acid in the $S_1$ subsite[7,8]. Deletion or mutation of the ced-3 gene completely prevented the apoptotic death of all cells that were otherwise destined to die, and both CED-3 as well as ICE induced apoptosis when transfected into a variety of host cells[6,9,10]. Furthermore, the pro-apoptotic effects of CED-3 could be prevented by co-transfection with the nematode death suppressor gene ced-9 and to some degree by its mammalian counterpart, the proto-oncogene bcl-2. The fate of eucaryotic cells may therefore reside in the balance between the opposing pro-apoptotic effects of an ICE/CED-3-like protease and an upstream regulatory mechanism involving Bcl-2 and/or its homologues.

One of the potential substrates for an ICE/CED-3-like protease during apoptosis is poly(ADP-ribose) polymerase (PARP), a key enzyme in DNA repair, genome surveillance and integrity[11-17]. PARP is proteolytically cleaved at the onset of apoptosis by a hitherto-unidentified protease with properties that resemble those of ICE[18,19]. The cleavage site within PARP ($DEVD^{216}$-$G^{217}$) resembles one of the two sites in proIL-1β ($FEAD^{27}$-$G^{28}$) that are recognized and cleaved by ICE. Proteolytic cleavage of PARP at this site results in the separation of the two zinc-finger DNA-binding motifs in the amino-terminus of PARP from the automodification and poly(ADP-ribos)ylating catalytic domains located in the carboxy-terminus of the polypeptide. This cleavage precludes the catalytic domain of PARP from being recruited to sites of DNA damage and presumably disables the ability of PARP to coordinate subsequent repair and genome maintenance events. Furthermore, the $Ca^{2+}/Mg^{2+}$-dependent endonuclease implicated in the internucleosomal DNA cleavage that is a hallmark of apoptosis is negatively regulated by poly(ADP-ribos)ylation[20-22]. Loss of normal PARP function would therefore render this nuclease highly activated in dying cells.

Interleukin-1β (IL-1β) is a major mediator of chronic and acute inflammation. It is synthesized as an inactive 31 kDa precursor (pIL-1β) that is processed to its mature 17.5 kDa form (mIL-1β) by interleukin-1β converting enzyme (ICE), a cysteine proteinase. Recently, a family of additional ICE-like genes has begun to emerge, including the namatode cell death abnormal gene (CED-3) of Caenorhabiditis elegans, Caenorhabiditis briggsae and Caenorhabiditis vulgaris, the murine neuronal precursor cell embroyonic developmentally downregulated (NEDD-2) gene and its human homologue ICH-1, as well as CPP32 which was cloned from Jurkat cells. We have cloned two additional novel human thiol proteinases which are related to ICE, designated $ICE_{rel}$-II (interleukin-1β converting enzyme-related cysteine proteinase II; U.S. Ser. No. 08/225,487, Filed Apr. 8, 1994) and $ICE_{rel}$-III (interleukin-1β converting enzyme—related cysteine proteinase III; U.S. Ser. No. 08/224,930, filed Apr. 8, 1994). The sequence identities of $ICE_{rel}$-II and $ICE_{rel}$-III with ICE are 61% and 56% respectively. All known sequences for ICE, CED-3 and other members of this new family of cysteine proteinases contain the pentapeptide sequence -Gln-Ala-Cys-Arg-Gly- surrounding the catalytic cysteine of ICE or its equivalent in the other members.

The five known members of the ICE/CED-3 family of cysteine proteases which are of human origin (ICE, $ICE_{rel}$-II, $ICE_{rel}$-III, ICH-1 and CPP32[23-26]) are each capable of initiating an apoptotic response when transfected into host cells; however, it is possible that overexpression of any protease may cause non-specific induction of cell death. Cytoplasmic expression of other proteases, such as trypsin, chymotrypsin, proteinase K or granzyme B, for example, have also been shown to induce apoptosis[27,28].

Herein we demonstrate that an active form of CPP32, designated apopain, is the enzyme responsible for the specific proteolytic breakdown of PARP that occurs at the onset of apoptosis. Furthermore, we show that inhibition of apopain-mediated PARP cleavage attenuates apoptosis in vitro, demonstrating the central role played by this protease in the apoptosis of mammalian cells.

As indicated immediately above, for purposes of this specification, the term 'apopain' is used herein to describe the enzymatically active form of the pro-apoptotic cyteine protease responsible for cleavage of poly(ADP-ribose) polymerase. The invention describes for the first time the identification of this enzyme and it is thus named apopain in accordance with I.U.B. nomenclature guidelines using the prefix 'apop' to indicate its role in apoptosis and the suffix 'ain' which is preferred by the I.U.B. for naming all cysteine proteases. The term CPP32 (cysteine protease protein of 32 kDa) is used to describe the inactive proenzyme from which apopain is derived or its corresponding cDNA.

Evidence suggests that the proteolytic activity of the ICE family of thiol proteinases, and more specifically by apopain, causes apoptosis at lease in part by disabling PARP. Therapeutics which selectively inhibit this cleavage would therefore sustain PARP activity and thus impede or prevent premature apoptotic cell death. Alternatively, therapeutics which enhance the activity of PARP cleavage thiol proteinases such as apopain would induce or accelerate apoptotic cell death.

SUMMARY OF THE INVENTION

In one aspect the present invention is directed to an isolated and purified enzyme designated apopain, methods of using apopain to screen for compounds which modulate the activity of apopain, and compounds identified by the screens. A synthetic DNA molecule encoding full length apopain is prepared based on the primary amino acid sequence of the purified enzyme. The synthetic apopain-encoding DNA is formulated so as to optimize expression in a variety of recombinant hosts. The DNA clones produce recombinant full-length apopain and derivatives thereof. Purified native apopain and recombinant apopain are useful for identifying modulators of apopain activity and hence modifiers of pathological conditions related to the pro-inflammatory or pro-apoptotic effects of apopain. Apopain antisense molecules are useful for therapeutically reducing or eliminating the pro-inflammatory or pro-apoptotic effects of apopain, whereas gene transplantation or gene therapy with apopain is useful for enhancing the pro-inflammatory or pro-apoptotic effects of apopain. These therapies are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease and Alzheimer's disease.

In a second aspect, this invention relates to substituted peptidyl derivatives of formula I

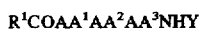

useful as research tools in the field of apoptosis, as well as in the treatment of diseases in which reduced apoptosis would be beneficial, including, but not limited to those listed above. In particular, this invention relates to inhibitors of the pro-apoptotic proteolytic activity of thiol proteinases which cause apoptosis at least in part by disabling the normal biological function of poly(ADP-ribose)polymerase.

BRIEF DESCRIPTION OF THE DRAWINGS

FIGS. 2a–d show inhibition of PARP cleavage in apoptotic osteosarcoma cell extracts.

FIGS. 5a–c show the kinetic analysis of apopain and a potent inhibitor using a flurogenic substrate.

FIGS. 6a–b show in vitro apoptosis and selective inhibition by Ac-DEVD-CHO or by depletion of apopain/CPP32-mediated PARP cleavage activity.

DETAILED DESCRIPTION OF THE INVENTION

Figure 1A:
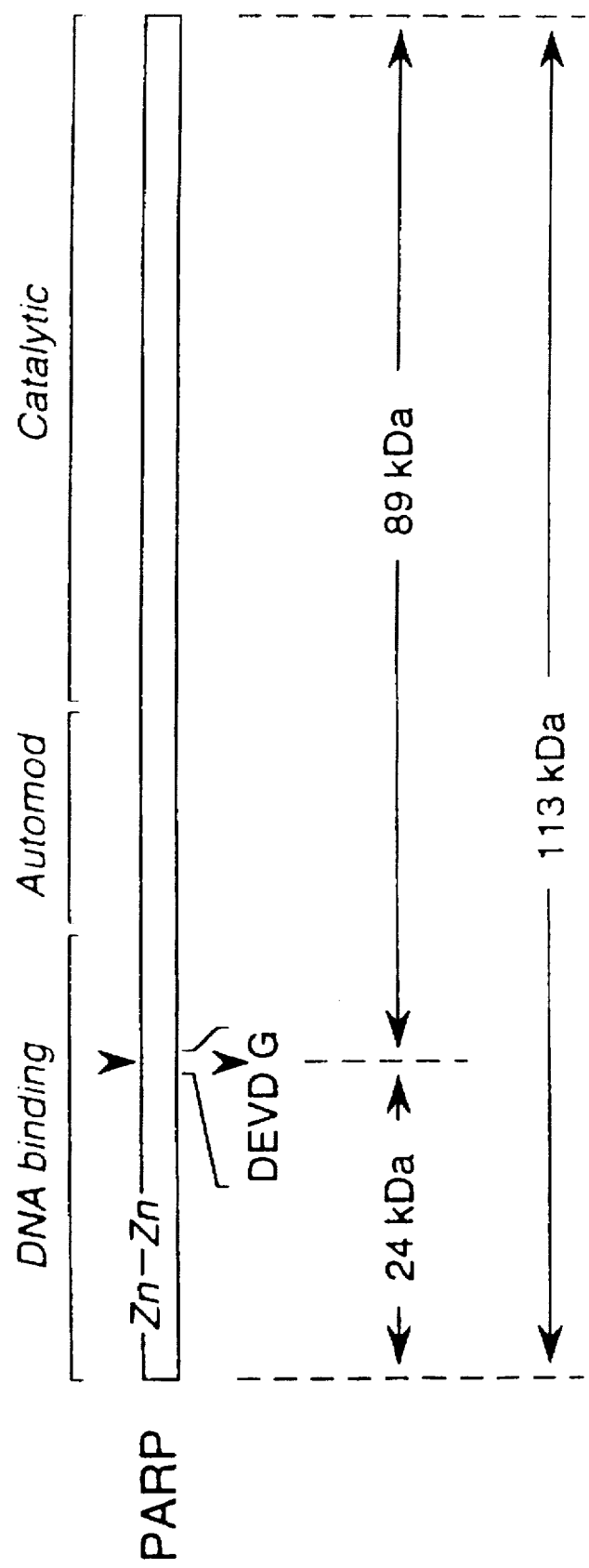
FIGS. 1a–d show PARP cleavage activity in spontaneously apoptotic osteosarcoma cells.

In one aspect, the present invention is directed to an isolated and purified enzyme designated apopain, methods of using apopain to screen for compounds which modulate the activity of apopain, and compounds identified by the screens. A synthetic DNA molecule encoding full length apopain is prepared based on the primary amino acid sequence of the purified enzyme. The synthetic apopain-encoding DNA is formulated so as to optimize expression in a variety of recombinant hosts. The DNA clones produce recombinant full-length apopain and derivatives thereof. Purified native apopain and recombinant apopain are useful for identifying modulators of apopain activity and hence modifiers of pathological conditions related to the pro-inflammatory or pro-apoptotic effects of apopain. Apopain antisense molecules are useful for therapeutically reducing or eliminating the pro-inflammatory or pro-apoptotic effects of apopain, whereas gene transplantation or gene therapy with apopain is useful for enhancing the pro-inflammatory or pro-apoptotic effects of apopain. These therapies are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease and Alzheimer's disease.

Apoptosis constitutes a systematic means of cell suicide within an organism during normal morphogenesis, tissue remodelling as well as in response to pathogenic infections or other irreparable cell damage. Inappropriate apoptosis may underlie the aetiology of human diseases such as Alzheimer's, Parkinson's and Huntington's diseases, immune deficiency and autoimmune disorders, ischemic cardiovascular and neurological injury, alopecia, leukemias, lymphomas and other cancers, which therefore makes the control of apoptosis an important potential target for therapeutic intervention[1-4].

Several of the biochemical events that contribute to apoptotic cell death have recently been elucidated. Genetic evidence in nematodes, for example, has identified both positive and negative regulators of apoptosis[5]. The key pro-apoptotic gene, ced-3, encodes a putative cysteine protease which is related to mammalian interleukin-1β converting enzyme (ICE)[6,] the first identified member of a new family of cysteine proteases with the distinguishing feature of a near absolute specificity for aspartic acid in the $S_1$ subsite[7,8]. Deletion or mutation of the ced-3 gene completely prevented the apoptotic death of all cells that were otherwise destined to die, and both CED-3 as well as ICE induced apoptosis when transfected into a variety of host cells[6,9,10]. Furthermore, the pro-apoptotic effects of CED-3 could be prevented by co-transfection with the nematode death suppressor gene ced-9 and to some degree by its mammalian counterpart, the proto-oncogene bcl-2. The fate of eucaryotic cells may therefore reside in the balance between the opposing pro-apoptotic effects of an ICE/CED-3-like protease and an upstream regulatory mechanism involving Bcl-2 and/or its homologues.

One of the potential substrates for an ICE/CED-3-like protease during apoptosis is poly(ADP-ribose) polymerase (PARP), a key enzyme in DNA repair, genome surveillance and integrity[11-17]. PARP is proteolytically cleaved at the onset of apoptosis by a hitherto-unidentified protease with properties that resemble those of ICE[18,19]. The cleavage site within PARP (DEVD[216]-G[217]) resembles one of the two sites in proIL-1β (FEAD[27]-G[28]) that are recognized and cleaved by ICE. Proteolytic cleavage of PARP at this site results in the separation of the two zinc-finger DNA-binding motifs in the amino-terminus of PARP from the automodification and poly(ADP-ribos)ylating catalytic domains located in the carboxy-terminus of the polypeptide. This cleavage precludes the catalytic domain of PARP from being recruited to sites of DNA damage and presumably disables the ability of PARP to coordinate subsequent repair and genome maintenance events. Furthermore, the $Ca^{2+}/Mg^{2+}$-dependent endonuclease implicated in the internucleosomal DNA cleavage that is a hallmark of apoptosis is negatively regulated by poly(ADP-ribos)ylation[20-22]. Loss of normal PARP function would therefore render this nuclease highly activated in dying cells.

The five known members of the ICE/CED-3 family of cysteine proteases which are of human origin are ICE, ICE$_{rel}$-II, ICE$_{rel}$-III, ICH-1 and CPP32[23-26]. Each is capable of initiating an apoptotic response when transfected into host cells; however, it is possible that overexpression of any protease may cause non-specific induction of cell death. Cytoplasmic expression of other proteases, such as trypsin, chymotrypsin, proteinase K or granzyme B, for example, have also been shown to induce apoptosis[27,28].

In this study we demonstrate that an active form of CPP32, apopain, is the enzyme responsible for the specific proteolytic breakdown of PARP that occurs at the onset of apoptosis. Furthermore, we show that inhibition of apopain-mediated PARP cleavage attenuates apoptosis in vitro, demonstrating the central role played by this protease in the apoptosis of mammalian cells.

In the nematode C. elegans, deletion or mutation of a single gene, ced-3, abolishes apoptotic death[5]. When sequenced, ced-3 was found to be homologous to the gene for mammalian interleukin-1β converting enzyme (ICE)[6], which encodes a protease whose only known function is the cleavage of the inactive 31 kDa proIL-1β cytokine precursor to the active 17 kDa form. How the apoptotic role of an ICE-like protease in mammalian cells can be accounted for, given the commitment of ICE to IL-1β formation and the finding that apoptosis occurs normally in ICE-deficient mice[29], has become more obvious with the discovery of four other mammalian ICE/CED-3-like proteases (ICE$_{rel}$-II, ICE$_{rel}$-III, ICH-1 and CPP32)[23-26] and the observation that poly(ADP-ribose) polymerase (PARP), a key enzyme in the coordination of genome structure and integrity, is functionally inactivated by a protease resembling ICE (prICE) at the onset of apoptosis[19]. We have demonstrated that prICE is in fact apopain/CPP32 and that apopain/CPP32 is the specific ICE/CED-3-like cysteine protease that cleaves PARP in mammalian cells. The central role played by apopain/CPP32 in mammalian cell death is further substantiated by potent and selective inhibitors which prevent apoptosis from occurring in vitro. These findings together with the sequence relationship between the apopain proenzyme, CPP32, and CED-3 suggests that CPP32 and its proteolytically active form, apopain, may be the human equivalent of CED-3. The pharmacological modulation of apopain activity may therefore be an appropriate point for therapeutic intervention in pathological conditions where inappropriate apoptosis is prominent.

The cloned apopain cDNA may be recombinantly expressed by molecular cloning into an expression vector containing a suitable promoter and other appropriate transcription regulatory elements, and transferred into prokaryotic or eukaryotic host cells to produce recombinant apopain.

Expression vectors are defined herein as DNA sequences that are required for the transcription of cloned copies of genes and the translation of their mRNAs in an appropriate host. Such vectors can be used to express eukaryotic genes in a variety of hosts such as bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant apopain in mammalian cells. Commercially-available mammalian expression vectors which may be suitable for recombinant apopain expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

DNA encoding apopain may also be cloned into an expression vector for expression in a recombinant host cell. Recombinant host cells may be prokaryotic or eukaryotic, including but not limited to bacteria, yeast, mammalian cells and insect cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are clonally propagated and individually analyzed to determine whether they produce apopain protein. Identification of apopain expressing host cell clones may be done by several means, including but not limited to immunological reactivity with anti-apopain antibodies, and the presence of host cell-associated apopain activity.

Expression of apopain cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the apopain cDNA sequence(s) that yields optimal levels of enzymatic activity and/or apopain protein, modified apopain cDNA molecules are constructed. Host cells are transformed with the cDNA molecules and the levels of apopain RNA and protein are measured.

Levels of apopain protein in host cells are quantitated by a variety of methods such as immunoaffinity and/or ligand affinity techniques. apopain-specific affinity beads or apopain-specific antibodies are used to isolate $^{35}$S-methionine labelled or unlabelled apopain protein. Labelled apopain protein is analyzed by SDS-PAGE. Unlabelled apopain protein is detected by Western blotting, ELISA or RIA assays employing apopain specific antibodies.

Following expression of apopain in a recombinant host cell, apopain protein may be recovered to provide apopain in active form. Several apopain purification procedures are available and suitable for use. Recombinant apopain may be purified from cell lysates or from conditioned culture media, by various combinations of, or individual application of fractionation, or chromatography steps that are known in the art.

In addition, recombinant apopain can be separated from other cellular proteins by use of an immuno-affinity column made with monoclonal or polyclonal antibodies specific for full length nascent apopainor polypeptide fragments of apopain The recombinant protein may be used to generate antibodies. The term "antibody" as used herein includes both polyclonal and monoclonal antibodies, as well as fragments thereof, such as, Fv, Fab and F(ab)2 fragments that are capable of binding antigen or hapten.

Monospecific antibodies to apopain are purified from mammalian antisera containing antibodies reactive against apopain or are prepared as monoclonal antibodies reactive with apopain using standard techniques. Monospecific antibody as used herein is defined as a single antibody species or multiple antibody species with homogenous binding characteristics for apopain. Homogenous binding as used herein refers to the ability of the antibody species to bind to a specific antigen or epitope, such as those associated with the apopain, as described above. Enzyme-specific antibodies are raised by immunizing animals such as mice, rats, guinea pigs, rabbits, goats, horses and the like, with rabbits being preferred, with an appropriate concentration of apopain either with or without an immune adjuvant.

Monoclonal antibodies (mAb) reactive with apopain may be prepared by conventional methods, such as by immunizing inbred mice with apopain. The mice are immunized with about 0.1 mg to about 10 mg, preferably about 1 mg, of apopain in about 0.5 ml buffer or saline incorporated in an equal volume of an acceptable adjuvant. Freund's complete adjuvant is preferred. The mice receive an initial immunization on day 0 and are rested for about 3 to about 30 weeks. Immunized mice are given one or more booster immunizations of about 0.1 to about 10 mg of apopain in a buffer solution such as phosphate buffered saline (PBS) by the intravenous (IV) route. Lymphocytes from antibody-positive mice are obtained by removing spleens from immunized mice by standard procedures known in the art. Hybridoma cells are produced by mixing the splenic lymphocytes with an appropriate fusion partner under conditions which will allow the formation of stable hybridomas. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using apopain as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

In vitro production of anti-apopain is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of apopain in body fluids or tissue and cell extracts.

Methods such as those described above may be used to produce monospecific antibodies may be utilized to produce antibodies specific for apopain polypeptide fragments or full-length nascent apopain polypeptide.

Apopain antibody affinity columns are made by adding the antibodies to a gel support, such as Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing apopain or apopain fragments are slowly passed through the column. The column is then washed, and the protein is eluted. The purified apopain protein is then dialyzed against phosphate buffered saline.

Kits containing apopain cDNA, antibodies to apopain or apopain protein may be prepared. Such kits are used to detect DNA which hybridizes to apopain DNA or to detect the presence of apopain protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of apopain DNA, apopain RNA or apopain protein. The recombinant proteins, DNA molecules, RNA molecules and antibodies lend themselves to the formulation of kits suitable for the detection and typing of apopain. Such a kit would comprise a compartmentalized carrier suitable to hold in close confinement at least one container. The carrier would further comprise reagents such as recombinant apopain protein or anti-apopain antibodies suitable for detecting apopain. The carrier may also contain means for detection such as labeled antigen or enzyme substrates or the like.

Nucleotide sequences that are complementary to the apopain encoding cDNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other apopain antisense oligonucleotide mimetics. Apopain antisense molecules may be introduced into cells by microinjection, liposome encapsulation or by expression from vectors harbouring the antisense sequence. apopain antisense therapy may be particularly useful for the treatment of diseases where it is beneficial to reduce apopain activity.

Apopain gene therapy may be used to introduce apopain into the cells of target organs. The apopain gene can be ligated into viral vectors which mediate transfer of the apopain DNA by infection of recipient host cells. Suitable viral vectors include retrovirus, adenovirus, adeno-associated virus, herpes virus, vaccinia virus, polio virus and the like. Alternatively, apopain DNA can be transferred into cells for gene therapy by non-viral techniques including receptor-mediated targetted DNA transfer using ligand-DNA conjugates or adenovirus-ligand-DNA conjugates, lipofection membrane fusion or direct microinjection. These procedures and variations of them are suitable for ex vivo as well as in vivo apopain gene therapy. apopain gene therapy may be particularly useful for the treatment of diseases where it is beneficial to elevate apopain activity.

Pharmaceutically useful compositions comprising apopain DNA or apopain protein may be formulated as described elsewhere in this application or according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein or DNA.

Therapeutic or diagnostic compositions of the invention are administered to an individual in amounts sufficient to treat or diagnose apopain related disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate.

As used herein, a "functional derivative" of apopain is a compound that possesses a biological activity (either functional or structural) that is substantially similar to the biological activity of apopain. The term "functional derivatives" is intended to include the "fragments," "variants," "degenerate variants," "analogs" and "homologs" or to "chemical derivatives" of apopain. The term "fragment" is meant to refer to any polypeptide subset of apopain. The term "variant" is meant to refer to a molecule substantially similar in structure and function to either the entire apopain molecule or to a fragment thereof. A molecule is "substantially similar" to apopain if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire apopain molecule or to a fragment thereof.

The term "chemical derivative" describes a molecule that contains additional chemical moieties which are not normally a part of the base molecule. Such moieties may improve the solublity, half-life, absorption, etc of the base molecule. Alternatively the moieties may attenuate undesirable side effects of the base molecule or decrease the toxicity of the base molecule. Examples of such moieties are described in a variety of texts, such as Remington's Pharmaceutical Sciences.

The present invention is also directed to methods for screening for compounds which modulate that expression of DNA or RNA encoding apopain as well as the function of apopain protein in vivo. Compounds which modulate these activities may be DNA, RNA, peptides, proteins, or non-proteinaceous organic molecules. Compounds may modulate by increasing or attenuating the expression of DNA or RNA encoding apopain or the function of apopain protein. Compounds that modulate the expression of DNA or RNA encoding apopain or the function of apopain protein may be detected by a variety of assays. The assay may be a simple "yes/no" assay to determine whether there is a change in expression or function. The assay may be made quantitative by comparing the expression or function of a test sample with the levels of expression or function in a standard sample.

In a second aspect, the invention encompasses compounds of formula I.

$$R^1COAA^1AA^2AA^3NHY \quad\quad I$$

or a pharmaceutically acceptable salt thereof:
wherein Y is:

$$-CH(CH_2CO_2H)(CO)_mR^2$$

m is 0, 1 or 2;
$R^1$ is
  (a) hydrogen, $C_{1-6}$ alkoxy, $NR^{10}R^{11}$, benzyloxy or mono- or disubstituted benzyloxy, wherein the substituent is methyl, halogen, methoxy or cyano, wherein $R^{10}R^{11}$ are independently $C_{1-4}$ alkyl, $C_{1-4}$ perfluoroalkyl, benzyl, mono or disubstituted benzyl wherein the substituent is halogen, methoxy or cyano, or $R^{10}$ and $R^{11}$ may be joined to form a pyrrolidine, piperidine, morpholine, thiamorpholine or N-$R^{12}$ substituted piperazine wherein $R^{12}$ is H or $C_{1-3}$ alkyl,
  (b) $C_{1-6}$ alkyl or substituted $C_{1-6}$ alkyl, wherein the substituent is selected from
    (1) hydroxy,
    (2) halo,
    (3) $C_{1-3}$ alkloxy,
    (4) $C_{1-3}$ alkylthio,
    (5) phenyl $C_{1-3}$ alkyloxy,
    (6) phenyl $C_{1-3}$ alkylthio,
    (7) phenylcarboxy, and
    (8) carboxy
  (c) aryl $C_{1-6}$ alkyl wherein the aryl group is selected from the group consisting of:
    (1) phenyl,
    (2) naphthyl,
    (3) pyridyl,
    (4) furyl,
    (5) thienyl,
    (6) thiazolyl,
    (7) isothiazolyl,
    (8) imidazolyl,
    (9) benzimidazolyl,
    (10) pyrazinyl,
    (11) pyrimidyl,
    (12) quinolyl,
    (13) isoquinolyl,
    (14) benzofuryl,
    (15) benzothienyl,
    (16) pyrazolyl,
    (17) indolyl,

(18) purinyl,
(19) isoxazolyl, and
(20) oxazolyl,
and mono and di-substituted aryl as defined above in items (1) to (20) wherein the substituents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl, carboxy, $C_{1-6}$alkloxycarbonyl;

$R^2$ is
  (a) hydrogen, $C_{1-6}$alkyl.OH, $C_{1-6}$alkoxy, $C_{1-6}$alkylthio, $C_{1-6}$perfluoroalkyl, $NR^{13}R^{14}$ wherein $R^{13}R^{14}$ are independently $C_{1-4}$ alkyl, $C_{1-4}$ perfluoroalkyl, benzyl, mono or disubstituted benzyl wherein the substituent is halogen, methoxy or cyano, or $R^{13}$ and $R^{14}$ may be joined to form a pyrrolidine, piperidine, morpholine, thiamorpholine or N-$R^{15}$ substituted piperazine wherein $R^{15}$ is H or $C_{1-3}$ alkyl,
  (b) tetra or penta substituted phenyl wherein the substituents are individually selected from the group consisting of
    (1) $C_{1-3}$alkylthio,
    (2) $C_{1-3}$alkoxy,
    (3) halo,
    (4) hydroxy,
    (5) cyano,
    (6) carboxy,
    (7) $C_{1-3}$alkyl,
    (8) trifluormethyl,
    (9) trimethylamino,
    (10) benzyloxy,
  (c) aryl wherein the aryl is selected from the group consisting of phenyl, 1-napthyl, 2-naphthyl, 9-anthracyl and 2, 3, or 4 pyridyl, and mono-, di or tri-substituted derivatives thereof, wherein the substituents are individually selected from the group consisting of
    (1) phenyl,
    (2) halo,
    (3) $C_{1-3}$alkyl,
    (4) perfluoro $C_{1-3}$alkyl,
    (5) nitro,
    (6) cyano,
    (7) $C_{1-3}$alkylcarbonyl,
    (8) phenylcarbonyl,
    (9) carboxy,
    (10) aminocarbonyl,
    (11) mono and di $C_{1-3}$alkylaminocarbonyl,
    (12) formyl,
    (13) $SO_3H$,
    (14) $C_{1-3}$alkyl sulfonyl,
    (15) phenyl sulfonyl,
    (16) formamido,
    (17) $C_{1-3}$alkylcarbonylamino,
    (18) phenylcarbonylamino,
    (19) $C_{1-3}$alkoxycarbonyl,
    (20) $C_{1-3}$alkylsulfonamido carbonyl,
    (21) phenylsulfonamido carbonyl,
    (22) $C_{1-3}$alkyl carbonylamino sulfonyl,
    (23) phenylcarbonylamino sulfonyl,
    (24) $C_{1-3}$alkyl amino,
    (25) mono or di $C_{1-3}$alkyl amino,
    (26) amino,
    (27) hydroxy,
    (28) $C_{1-3}$alkyloxy,
    (29) $C_{1-3}$alkythio; and
$AA^1$ is independently selected from the group consisting of
  (a) a single bond, and
  (b) an amino acid of formula AI

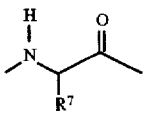

$AA^2$ is an amino acid of formula AII

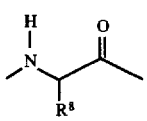

$AA^3$ is an amino acid of formula AIII

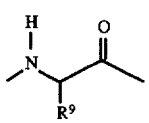

wherein $R^7$, $R^8$ and $R^9$ are each independently selected from the group consisting of
  (a) (b) hydrogen,
  (b) $C_{1-6}$alkyl or substituted $C_{1-6}$alkyl, wherein the substituent is selected from
    (1) hydroxy,
    (2) halo,
    (3) —S—$C_{1-4}$alkyl,
    (4) —SH
    (5) $C_{1-6}$alkylcarbonyl,
    (6) $CO_2H$,
    (7) $CONH_2$,
    (8) amino carbonyl amino,
    (9) $C_{1-4}$alkylamino, wherein the alkyl moiety is optionally substituted with hydroxy, and the amino is substituted with hydrogen or CBZ,
    (10) guanidino,
    (11) $C_{1-4}$alkyloxy,
    (12) phenyl $C_{1-4}$alkyloxy,
    (13) phenyl $C_{1-4}$alkylthio,
    (14) $C_{1-6}$alkyloxycarbonyl, and
  (c) aryl $C_{1-6}$ alkyl,
wherein aryl is phenyl, 1- or 2-naphthyl, 9-authracyl, or 2-, 3- or 4-pyridyl, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

One class of this genus is the compounds wherein:
$R^1$ is
  (a) hydrogen, $C_{1-6}$alkoxy, mono or disubstituted benzyloxy wherein the substituent is methyl, halogen, methoxy or cyano,
  (b) $C_{1-6}$ alkyl or substituted $C_{1-6}$ alkyl, wherein the substituent is selected from
    (1) hydroxy,
    (2) chloro, fluoro,
    (3) $C_{1-3}$ alkyloxy,
    (4) phenyl $C_{1-3}$ alkyloxy,
    (5) phenylcarboxy, and
    (6) carboxy.
  (c) aryl $C_{1-6}$ alkyl wherein the aryl group is selected from the group consisting of:
    (1) phenyl,
    (2) naphthyl,
    (3) pyridyl,
    (4) furyl, (5) thienyl,
(6) thiazolyl,
(7) isothiazolyl,
(8) benzofuryl,
(9) benzothienyl,
(10) indolyl,
(11) isoxazolyl, and
(12) oxazolyl, and mono and di-substituted aryl as defined above in items (1) to (12) wherein the substituents are independently $C_{1-4}$alkyl, hydroxy, carboxy, $C_{1-6}$alkyloxycarbonyl, halo;

$R^2$ is (a) hydrogen, OH, $C_{1-6}$ alkyloxy or $C_{1-6}$ perfluoroalkyl;

$R^7$, $R^8$ and $R^9$ are each independently selected from the group consisting of
(a) hydrogen,
(b) substituted $C_{1-6}$ alkyl, wherein the substituent is selected from
  (1) hydrogen,
  (2) hydroxy,
  (3) halo,
  (4) —S—$C_{1-4}$alkyl,
  (5) —SH
  (6) $C_{1-6}$ alkylcarbonyl,
  (7) $CO_2H$,
  (8) —$CONH_2$,
  (9) $C_{1-4}$ alkylamino, wherein the alkyl moiety is optionally substituted with hydroxy, and
  (10) guanidino, and
(c) aryl $C_{1-6}$ alkyl, wherein aryl is as defined previously, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

Within this class are the compounds wherein $AA^1$, $AA^2$ and $AA^3$, are each independently selected from the group consisting of the L- and D- forms of the amino acids including glycine, alanine, valine, leucine, isoleucine, serine, threonine, aspartic acid, asparagine, glutamic acid, glutamine, lysine, hydroxy lysine, histidine, arginine, phenylalanine, tyrosine, tryptophan, cysteine, methionine, ornithine, b-alanine, homoserine, homotyrosine, homophenylalanine and citrulline.

Alternatively, within the class are the subclass of compounds wherein:

$R^1$ is $C_{1-3}$alkyl, $C_{1-4}$alkoxy;

$R^8$ and $R^9$ are each individually
(a) hydrogen,
(b) $C_{1-6}$alkyl or substituted $C_{1-6}$alkyl, wherein the substituent is selected from
  (1) hydroxy,
  (2) SH
  (3) $CO_2H$
  (4) $CONH_2$, and
  (5) guanidino.

Exemplifying the invention are the following compounds:

(a) N-(N-Acetyl-aspartyl-glutamyl-valinyl)-3-amino-3-formylpropionic acid
(b) N-(N-(1,1-Dimethylethoxycarbonyl)-aspartyl-glutamyl-valinyl)-3-amino-formylpropionic acid
(c) N-(N-(1,1-Dimethylethoxycarbonyl)-aspartyl-glutamyl-valinyl)-3-amino-3-(trifluoromethylcarbonyl)propionic acid
(d) N-(N-(N-(1,1-Dimethylethoxycarbonyl)anthranilyl)-aspartyl-glutamyl-valinyl)-3-amino-3-formylpropionic acid
(e) N-(N-(3-(2-oxo-hexahydro-thieno[3,4-d]imidazol-4-yl)pentanoyl)-aspartyl-glutamyl-valinyl)-3-amino-3-formylpropionic acid
(f) N-(N-(N-(5-(3a-(S)-6a-(R)-2-oxo-hexahydro-thieno [3,4-d]imidazol-4-yl)pentanoyl)-6-aminohexanoyl)-aspartyl-glutamyl-valinyl)-3-amino-3-formylpropionic acid.

For purposes of this specification, the following abbreviations have the indicated meanings:

BOC=t-butlyoxycarbonyl
CBZ=carbobenzoxy
DCC=1,3-dicyclohexylcarbodiimide
DIBAL=diisobutyl aluminum hydride
DMAP- 4-(dimethylamino)pyridine
DMF=N,N-dimethylformamide
DMSO=dimethyl sulfoxide
EDCI=1-(3-dimethylaminopropyl)-3-ethylcarbodiimide hydrochloride
$Et_3N$=triethylamine
EtOAc=ethyl acetate
$Et_2O$=ethyl ester
FAB=fast atom bombardment
HMPA=hexamethylphosphoramide
HOBt=1-hydroxybenzotriazole
HRMS=high resolution mass spectrometry
KHMDS=potassium hexamethyldisilazane
LDA=lithium diisopropylamide
MCPBA=metachloroperbenzoic acid
Ms=methanesulfonyl=mesyl
MsO=methanefulfonate=mesylate
NBS=N-bromosuccinimide
PCC=pyridinium chlorochromate
PDC=pyridinium dichromate
Ph=phenyl
PPTS=pyridinium p-toluene sulfonate
pTSA=p-toluene sulfonic acid
Pye=pyridinediyl
r.t.=room temperature
rac.=racemic
Tf=trifluoromethanesulfonyl=triflyl
TfO=trifluoromethanesulfonate=triflate
THF=tetrahydrofuran
THP=tetrahydropyran-2-yl
TLC=thin layer chromatography
Ts=p-toluenesulfonyl=tosyl
TsO=p-toluenesulfonate=tosylate
Tz=1H (or 2H)-tetrazol-5-yl
Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl The term alkyl, means linear, branched, and cyclic structures and combinations thereof, with the number of carbon atoms indicated by the prefix.

"Alkoxy" means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

"Alkylthio" means alkylthio groups of the indicated number of carbon atoms of a straight, branched, or cyclic configuration. Examples of alkylthio groups include methylthio, propylthio, isopropylthio, cycloheptylthio, etc. By way of illustration, the propylthio group signifies —SCH₂CH₂CH₃.

Halo includes F, Bl, Br, and I.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The ability of the compounds of Formula I to inhibit the action of apopain make them useful research tools in the field of apoptosis. These compounds are also useful to treat, prevent, or ameliorate in mammals and especially in humans, diseases including but not limited to:

1. immune dificiency syndrome (including AIDS)
2. type I diabetes
3. pathogenic infections
4. cardiovascular and neurological injuries
5. alopecia
6. aging
7. Parkinson's disease
8. Alzheimer's disease Dose Ranges The magnitude of therapeutic dose of a compound of Formula I will, of course, vary with the nature of the severity of the condition to be treated and with the particular compound of Formula VI and its route of administration and vary upon the clinician's judgement. It will also vary according to the age, weight and response of the individual patient. An effective dosage amount of the active component can thus be determined by the clinician after a consideration of all the criteria and using is best judgement on the patient's behalf.

An ophthalmic preparations for ocular administration comprising 0.001–1% by weight solutions or suspensions of the compounds of Formula I in an acceptable ophthalmic formulation may be used.

Pharmaceutical Compositions

Any suitable route of administration may be employed for providing a mammal, especially a human with an effective dosage of a compound of the present invention. For example, oral, parenteral and topical may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, parenteral and ocular (ophthalmic). They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, alcohols, oils, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case or oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy but all methods include the step of bringing into active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Methods of Synthesis

Compounds of the instant invention are conveniently prepared using the procedures described generally below and more explicitly described in the Example section thereafter.

Method A

A N-protected amino acid 1, with a group such as a BOC, CBZ or any other suitable nitrogen protecting group is converted to an allyl ester by a coupling reaction with 1-(-3-dimethylaminopropyl)-3-ethylcarbodiimide hydrochloride (EDCI) in an inert solvent such as $CH_2Cl_2$ or $CHCl_3$ at 0° C. with allyl alcohol to yield 2. This amino acid is N-deprotected with an acid such as HBr in MeOH in the case where the nitrogen was protected by a BOC group to yield the free amine. With a different group the deprotection use is described in "Protective groups in Organic Synthesis" 2nd ed. Wiley and Sons, N.Y., 1991. The amine is coupled as described above with 3 to yield the dipeptide 4. After deprotection of the amine according to the previous conditions, it is coupled with 5 to yield the tripeptide 6. The BOC group on 5, can also be replaced by a fluorogenic substrate such as a 2-t-butyloxy- carbonylamino benzoate. Deprotection of the allyl group with palladium (0) and pyrrolidine ("Tetrahedron Lett." 1987, 28, 4371) affords the acid which is coupled with n-allyloxycarbonyl-4-amino-5-benzyloxy-2-oxotetrahydrofuran 7 according to "Bio. Med. Chem. Lett." 1992, 2, 613, to yield 8 after benzyl deprotection under reductive conditions. $R^2$ in 7 could be an H, $CH_3$, $CF_3$, OMe and SMe.

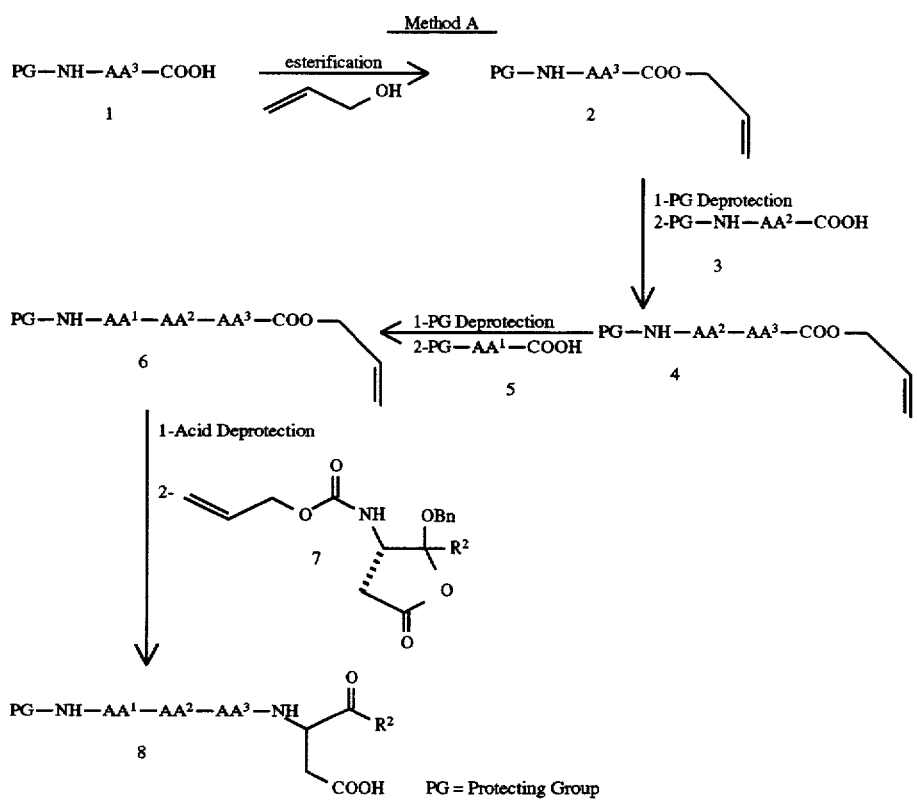

Assays for Determining Biological Activity

Measurement of proteolytic cleavage of poly(ADP-ribose)polymerase (a) Preparation of [$^{35}$S] radiolabelled PARP The cDNA encoding human poly(ADP-ribose) polymerase (clone pCD-12; GenBank accession no. M32721; NCBI gi 190266) was excised from its cloning vector by Xho I restriction digestion then ligated into Xho I-cut, CIP-treated pBluescript II SK+ (Stratagene). Following transformation into competent Escherichia coli cells, colony purification and propagation of the resulting transformed cells in liquid culture, the plasmid DNA was purified and the orientation of the PARP cDNA was determined by restriction enzyme analysis. Clones oriented in the T7 as well as T3 directions were obtained and their plasmid DNA was used to direct the synthesis of [$^{35}$S]PARP by coupled in vitro transcription/translation using TnT reticulocyte lysates (Promega) in the presence of [³⁵S]methionine (New England Nuclear). The resulting [³⁵S]PARP polypeptide was purified away from the constituents of the reticulocyte lysate mixture by gel filtration chromatography on a Superdex-75 HR 10/30 column (Pharmacia) which had been equilibrated in 10 mM Hepes/KOH (pH 7.4), 2 mM EDTA, 0.1% CHAPS, 5 mM dithiothreitol.

(b) Measurement of PARP cleavage

Incubation mixtures (25 μl final volume) were prepared in a buffer composed of 10 mM Hepes/KOH (pH 7.4), 2 mM EDTA, 0. 1% CHAPS, 5 mM dithiothreitol and contained 5 μl of purified [³⁵S]PARP, 0-10 μl of PARP cleavage activity (eg., fractions from apoptotic osteosarcoma,THP-1 or other cells, or purified apopain or recombinant apopain) plus drug, where indicated, or vehicle. The mixtures were incubated for 60 min at 37° C. then terminated by the addition of 6.5 μl of 5-fold concentrated SDS-containing PAGE sample buffer followed by denaturation for 5 min at 95° C. The samples were resolved on 10% polyacrylamide gels, transferred to a poly(vinylidene difluoride) membrane by electroblotting, then the [³⁵S]PARP cleavage products were visualized by autoradiography. PARP cleavage was measured as the breakdown of the 113.1 kDa PARP polypeptide into 24.1 kDa and 89.1 kDa fragments. PARP cleavage activity was quantified by the volume-density of the 24.1 kDa fragment as determined by laser densitometry of the resulting autoradiogram.

(c) Measurement of PARP cleavage by cleavage of a fluorogenic substrate

A fluorogenic derivative of the tetrapeptide recognized by apopain and corresponding to the $P_1$ to $P_4$ amino acids of the PARP cleavage site, Ac-DEVD-AMC (AMC, amino-4-methylcoumarin) was prepared as follows: i) synthesis of N-Ac-Asp(OBn)-Glu(OBn)-Val-$CO_2$H, ii) coupling with Asp(OBn)-7-amino-4-methylcoumarin, iii) removal of benzyl groups.

and a central region where automodification occurs that subsequently alters DNA binding affinity[37]. The site of proteolytic cleavage that occurs at the onset of apoptosis is indicated by an arrowhead. b, In vitro cleavage of PARP by cell extracts. [³⁵S]PARP was generated by in vitro transcription/translation then combined with cytosolic extracts from pre-confluent, non-apoptotic osteosarcoma cells (lane 2), post-confluent, apoptotic osteosarcoma cells (lane3), freshly-isolated THP- 1 cells (lane 4), THP-1 cell extracts activated by pre-incubation for 60 min at 37° C. (lane 5) or apoptotic chicken S/M extracts (lane 6). c, Internucleosomal DNA cleavage in progressively apoptotic osteosarcoma cells. Osteosarcoma cells were maintained in culture for the indicated number of days and then harvested. DNA was extracted and resolved on agarose gels. An asterisk indicates the time point (day 6) where confluence was reached. d, Elevation of PARP cleavage activity in progressively apoptotic osteosarcoma cells. Cytosol fractions were isolated from progressively apoptotic osteosarcoma cells described in panel c then assayed for PARP cleavage activity (open circles) and proIL-1β cleavage activity (open squares). METHODS. b. Cytosolic extracts were prepared from cultured human osteosarcoma cells (143.98.2; ATCC CRL 11226) and THP-1 cells (ATCC TIB 202) by homogenizing PBS-washed cell pellets in 10 mM Hepes/KOH (pH 7.4), 2 mM EDTA, 0.1 % (w/v) CHAPS, 5 mM dithiothreitol, 1 mM phenylmethylsulfonylfluoride, 10 μg/ml pepstatin A, 20 μg/ml leupeptin, 10 μg/ml aprotinin (at $1\times10^8$ cells/ml) and recovering the supernatant after successive centrifugation at 1000×g, 10,000×g then 100, 000×g. Chicken S/M extracts were prepared from DU249 hepatoma cells[38] that were committed to apoptosis by S-phase aphidicolin arrest followed by M-phase accumulation with nocodazole as described previously[35]. The full length cDNA clone for PARP (pcD-12)[39] was excised and

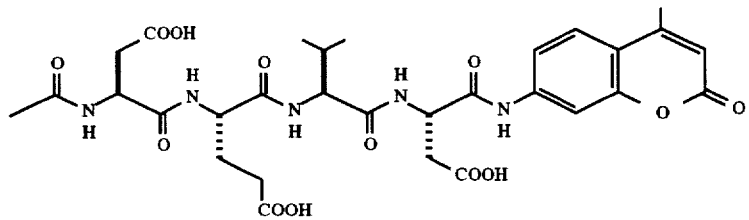

Standard reaction mixtures (300 μl final volume), contained Ac-DEVD-AMC and purified or crude PARP-cleavage apopain/CPP32 enzyme in 100 mM Hepes/KOH (pH 7.5), 10% (w/v) sucrose, 0.1% (w/v) CHAPS, 10 mM dithiothreitol, and were incubated at 25° C. Reactions were monitored continuously in a spectrofluorometer at an excitation wavelength of 380 nm and an emission wavelength of 460 nm.

The following examples illustrate the present invention without, however, limiting the same thereto.

DETAILED DESCRIPTION OF THE DRAWINGS

FIG. 1 shows PARP cleavage activity in spontaneously apoptotic osteosarcoma cells. a, Structure of PARP and fragments resulting from proteolytic cleavage. Poly(ADP-ribose) polymerase is a 113 kDa nuclear protein comprised of three functional domains: an amino-terminal DNA binding domain which contains two zinc-finger motifs that selectively recognize either single-stranded or double-stranded DNA breaks, a carboxy-terminal catalytic domain, ligated into the Xho I site of pBluescript-II SK+ (Stratagene) then used to drive the synthesis of [³⁵S]methionine-labelled PARP by coupled transcription (T7 polymerase)/translation (rabbit reticulocyte lysate) (Promega). [³⁵S]PARP was separated from the constituents of the transcription/translation mixture by gel filtration chromatography on a Superdex-75 FPLC column (Pharmacia; 1×30 cm) in 10 mM Hepes/KOH (pH 7.4), 2 mM EDTA, 0.1% (w/v) CHAPS, 5 mM dithiothreitol. Reaction mixtures containing [³⁵S]PARP (25μl final volume in 50 mM Pipes/KOH (pH 6.5), 2 mM EDTA, 0.1% (w/v) CHAPS, 5 mM dithiothreitol) were incubated for 1 hr at 37° C. in the absence (lane 1) or presence (lanes 2–6) of cytosolic extracts, including 4.5 μg protein from the cytosol fraction of non-apoptotic osteosarcoma cells (from 3 day, pre-confluent cultures) (lane 2), 4.5 μg protein from the cytosol fraction of apoptotic osteosarcoma cells (from 7 day, post-confluent cultures) (lane 3), 30 μg protein from the cytosol fraction of THP- 1 cells (lane 4), 30 μg protein from a THP- 1 cell cytosol fraction that was activated by pre-incubation for 60 min at 37° C.) (lane 5) or 0.6 μg protein from chicken S/M extracts (lane 6). Samples were resolved on 10% SDS/polyacrylamide gels and [$^{35}$S]PARP cleavage products were visualized by fluorography. c. Osteosarcoma cells were seeded at a density of 4000 cells/cm$^2$ and maintained in culture for the indicated period of time. The DNA from 1×10$^6$ cells for each time point was isolated by phenol/chloroform extraction, digestion with DNase-free RNase and alcohol precipitation then resolved on 1.2% agarose/TAE gels which were subsequently stained with ethidium bromide. d. Cytosol fractions from the cells described in panel c were isolated then assayed for PARP cleavage activity using [$^{35}$S]PARP (open circles) as described in panel b. PARP cleavage was quantified by laser densitometry of the 24 kDa band on the resulting fluorograms. Data are the average of two independent experiments. ICE activity (open squares) was measured by the cleavage of [$^{35}$S]proIL-1β essentially as described above for [$^{35}$S]PARP above except at pH 7.4.

FIG. 2 shows inhibition of PARP cleavage in apoptotic osteosarcoma cell extracts. a. Inhibition by various protease inhibitors. The cytosol fraction from apoptotic osteosarcoma cells was incubated with [$^{35}$S]PARP (derived by in vitro transcription/translation) in the presence of various protease inhibitors as indicated. The 24 kDa cleavage product from the resulting fluorogram is shown. b. Inhibition by synthetic tetrapeptide aldehydes. The cytosol fraction from apoptotic osteosarcoma cells was incubated with [$^{35}$S]PARP in the presence of the indicated concentrations of the tetrapeptide aldehyde Ac-DEVD-CHO (open circles) or Ac-YVAD-CHO (solid squares) which were modeled after the $P_1$-$P_4$ amino acids of the PARP cleavage site and proIL- 1β cleavage site, respectively. The structure of Ac-DEVD-CHO is shown in the inset.
METHODS. a. [$^{35}$S]PARP cleavage was measured as described in FIG. 1b except that i) the concentration of dithiothreitol was lowered from 5 mM to 1 mM in the chromatography of the transcription/translation mixture, the cell lysis buffer and the [$^{35}$S]PARP cleavage incubation buffer, and ii) the cell lysis buffer did not contain protease inhibitors. Incubation mixtures containing 10 µg protein from the cytosol fraction of apoptotic osteosarcoma cells (from 7 day, post-confluent cultures) were pre-incubated for 20 min at 37° C. with the indicated protease inhibitor before the addition of [$^{35}$S]PARP. The incubation was continued at 37° C. for 60 min then the samples were resolved on 10% SDS/polyacrylamide gels. Cleavage products were visualized by fluorography of the resulting dried gel and the region corresponding to the 24 kDa product is shown. Control samples were incubated in the absence of cytosol fraction (lanes 1 and 16) or presence of cytosol but absence of protease inhibitors (lanes 2 and 17). Incubation mixtures contained 100 µM 4-amidino-phenyl-methane-sulfonyl fluoride (pAPMSF; lane 3), 2 µg/ml aprotinin (lane 4), 100 µM elastinal (lane 5), 1 mM phenylmethylsulfonylfluoride (PMSF, lane 6), 100 µM L-1-chloro-3-[4-tosylamido]-7-amino-2-heptanone (TLCK, lane 7), 100 µM L-1-chloro-3-[4-tosylamido]-4-phenyl-2-butanone (TPCK, lane 8), 1 mg/ml soybean trypsin inhibitor (SB-TI, lane 9), 10 µM amastatin (lane 10), 10 µM bestatin (lane 11), 50 µM diprotin A (lane 12), 8.5 µM phosphoramidon (lane 13), 1 µM pepstatin (lane 14), 5 mM EDTA (lane 15), 1 mg/ml a2 macroglobulin (lane 18), 100 µM antipain (lane 19), 100 µM chymotrypsin (lane 20), 100 µM leupeptin (lane 21), 10 µM E-64 (lane 22), 5 mM iodoacetamide (lane 23), 5 mM N-ethylmaleimide (lane 24), 1 µM Ac-YVAD-CHO (lane 25), 100 nM Ac-DEVD-CHO (lane 26) or 100 nM Ac-DEVD-COOH (lane 27). Further controls contained the solvents used to introduce the inhibitors into reaction mixtures (which were prepared as fresh 50×stocks) which were water (lane 28; used for sample 3), methanol (lane 29; used for samples 7,8,11,14), ethanol (lane 30; used for samples 6,10) and dimethylsulfoxide (lane 31, used for samples 20,25–27). Stocks for the remainder were prepared in the incubation buffer. b. The tetrapeptide aldehyde Ac-YVAD-CHO was synthesized as described previously[40] and Ac-DEVD-CHO (inset) was synthesized essentially by the same procedure. [$^{35}$S]PARP cleavage activity was measured as described in FIG. 1b. Incubation mixtures containing 10 µg protein from the cytosol fraction of apoptotic osteosarcoma cells (from 7 day, post-confluent cultures) were pre-incubated for 20 min at 37° C. with the indicated concentrations of Ac-YVAD-CHO (solid squares) or Ac-DEVD-CHO (open circles) before the addition of [$^{35}$S]PARP. The incubation was continued at 37° C. for 60 min then the samples were resolved on 10% SDS/polyacrylamide gels. Cleavage products were visualized by fluorography of the resulting dried gel and the band corresponding to the 24 kDa cleavage product was quantified by laser densitometry. Data are expressed as the percentage of the control to which no inhibitor was added and are the average of two independent experiments.

FIG. 3 shows purification of the PARP cleavage protease from THP-1 cells. a. DEAE anion-exchange chromatography. b. Structure of biotinylated tetrapeptide-aldehyde affinity ligands. c. SDS/polyacrylamide gel electrophoresis of THP-1 cell cytosol fraction (lane 1), DEAE peak active fraction (fraction 114) before (lane 2) and after (lane 3) affinity chromatography, eluent from Biotin-DEVD-CHO (lane 5) and Biotin-[X]-DEVD-CHO (lane 6) affinity columns.
METHODS. a. The cytosol fraction from cultured THP-1 cells was isolated, dialysed and concentrated as described previously[41] then applied to a DEAE-5PW HPLC column (TosoHaas, 5.5×20 cm; 3–5 gm protein from 1.4×10$^{11}$ cells) that had been pre-equilibrated at 4° C. in 20 mM Tris/HCl (pH 7.8), 10% (w/v) sucrose, 0.1% (w/v) CHAPS, 2 mM dithiothreitol. Proteins were eluted with a linear gradient of 0.4M NaCl, 240 mM Tris/HCl (pH 7.8), 10% (w/v) sucrose, 0.1% (w/v) CHAPS, 2 mM dithiothreitol. Fractions corresponding to approximately 90 to 120 mM NaCl, which immediately followed those containing ICE activity, were pooled and the pools from 25 DEAE chromatography runs were combined (1.6 gm protein, from 3.5×10$^{12}$ THP-1 cells) and re-run under identical conditions. The PARP cleavage activity was assayed in each fraction as described in FIG. 1b and quantified by laser densitometry as described in FIG. 2b. Alternatively, activity was measured using the synthetic fluorogenic tetrapeptide-aminomethylcoumarin (Ac-DEVD-AMC) described in detail in FIG. 5. b. Biotin-DEVD-CHO and Biotin-[X]-DEVD-CHO differ by the presence of a 0.9 nm spacer arm (indicated by the square brackets) which is present in Biotin-[X]-DEVD-CHO but absent in Biotin-DEVD-CHO. These ligands were prepared by: i) synthesis of t-Boc-Asp(OBn)-Glu(OBn)-Val-Asp-CHO protected as the benzylated lactol at the aldehyde, ii) removal of the t-Boc group, iii) acylation of the free amine with biotin (for Biotin-DEVD-CHO) or biotinamidocaproic acid (for Biotin-[X]-DEVD-CHO) using EDCI and HOBt. This approach, using a biotinylated affinity ligand which could be subsequently immobilized on streptavidin-agarose (depicted in the inset), was chosen since i) the spacer arm length was readily varied, ii) the ligand concentration on the agarose beads could be precisely controlled, and iii) the biotinylated ligand could be pre-incubated with the enzyme to allow full equilibrium to be reached before harvesting the complex with streptavidin-agarose, a particular advantage owing to the time-dependent approach to equilibrium ($k_{on} > 10^5 M^{-1} s^{-1}$) of this class of ligands with the PARP cleavage enzyme. c. The fraction from DEAE chromatography corresponding to the peak of PARP cleavage activity (fraction 114; 2.5 ml containing 3 mg protein) was incubated with 20 nmol of Biotin-|X|-DEVD-CHO in a total volume of 10 ml of 50 mM PIPES/KOH (pH 6.8), 2 mM EDTA, 0.1 % (w/v) CHAPS, 5 mM dithiothreitol for 30 min at room temperature. The mixture was then passed through a streptavidin-agarose column (1 ml bed volume; pre-equilibrated in 50 mM PIPES/KOH (pH 6.8), 2 mM EDTA, 0.1 % (w/v) CHAPS, 5 mM dithiothreitol; binding capacity=63 nmol biotin/ml) and washed with 20 column volumes of the same buffer. The enzyme was eluted by perfusing the column with 2 mM D-biotin in the same buffer and allowing it to stand for several hours before recovering the purified PARP cleavage enzyme. An identical affinity chromatography run using Biotin-DEVD-CHO yielded comparable results. Samples were resolved on 14% SDS/polyacrylamide gels and protein bands were visualized by silver staining. Samples contained 9 µg protein from a THP-1 cell cytosol fraction (lane 1), 6 µg protein from DEAE fraction 114 before (lane 2) and after (lane 3) Biotin-[X]-DEVD-CHO affinity chromatography, and 0.1 µg protein from the eluent of Biotin-DEVD-CHO (lane 5) and Biotin-[X]-DEVD-CHO (lane 6) affinity columns.

FIG. 4 shows the structure of PARP cleavage protease; apopain, which is processed from the inactive proenzyme CPP32 a. Electrospray mass spectroscopy analysis of 17 kDa (left) and 12 kDa (right) subunits of the purified PARP cleavage protease. Numbers in brackets indicate the calculated masses of the subunits based on the sequences described in panel b. b. Primary structure of apopain/CPP32. The deduced amino acid sequence from the CPP32β cDNA clone[25] is shown. Hatched bars indicate the amino-terminal sequences determined for the purified enzyme subunits. Arrowheads mark the $Asp^{28}$-$Ser^{29}$ and $Asp^{175}$-$Ser^{176}$ cleavage sites which yield the p17 and p12 subunits from the CPP32 proenzyme. The conserved Gln-Ala-Cys-Arg-Gly pentapeptide containing the putative catalytic cysteine (star) is also boxed. c. Comparison of ICE and CPP32 pro-enzyme organization. Bars represent the p45 and p32 proenzymes for ICE and CPP32, respectively. The larger subunits, which contain the putative catalytic cysteine residues, and the smaller subunits are indicated by solid and hatched bars, respectively. d. Phylogenic relationship of all know members of the ICE/CED-3 family of cysteine proteases. e. Multiple sequence alignment of all known human ICE/CED-3-like proteases (top 5 sequences) and nematode CED-3 (bottom sequence). Numbering corresponds to the residue position within human ICE. Regions implicated in substrate binding to human ICE, based on the X-ray crystal structure[33,34], are shown: solid circles, catalytic; open circles, binding pocket for carboxylate of $P_1$ Asp; triangles, proximity (<0.4 nm) to $P_2$-$P_4$ residues. Arrowheads indicate known proenzyme cleavage sites for ICE and CPP32. METHODS. a. Aliquots of the purified PARP cleavage enzyme described in FIG. 3c were resolved on a narrow bore C4 reverse-phase HPLC column and the individual subunits were analyzed by capillary liquid chromatography coupled to a triple sector quadrapole mass spectrometer equipped with an electrospray ion source essentially as described before[7]. Tryptic peptides were also generated from the purified apopain subunits[40] and analyzed by electrospray mass spectroscopy to further substantiate identification. Peptides and their respective predicted and observed masses were: IPVEADFLYAYSTAPGYYSWR[207], 2470.8,2470.2; VATEFESFSFDATFHAK[259], 1935.1,1934.7; LEFMHILTR[238], 1160.4,1161.0; ELYFYH[277], 872.0, 872.0. b. Approximately 100 pmol of the purified PARP cleavage enzyme described in FIG. 3c was resolved on a 14% SDS/polyacrylamide and transferred to a polyvinylidenedifluoride membrane by electroblotting. Regions of the membrane containing the individual p17 and p12 subunits were excised and sequenced by conventional Edman degradation using a continuous-flow reactor (Sheldon Biotechnology Centre, Montreal Canada). Hatched bars represent the resulting amino-terminal sequences which perfectly corresponded to the deduced amino acid sequence of CPP32β. d.e. Deduced polypeptide sequences (entire open reading frame) for the indicated cDNA or gene sequences were aligned using the Genetics Computer Group (Madison WI) PILEUP algorithm[42] (gap weight=3.0; gaplength weight=0.1) and are presented as a phylogenic dendogram (d) or an amino acid alignment (e). $hICE_{rel}$-II and $hICE_{rel}$-III are human ICE-related cysteine protease II and III, respectively; mICE, rICE and hICE are murine, rat and human ICE (interleukin-1β converting enzyme), respectively; mNedd2 and hICH-1 are the murine and human forms of $Nedd2/ICH-1_L$, respectively; cbCED-3, cvCED-3 and ceCED-3 are *Caenorhabditis briggsae*, *vulgaris* and *elegans* CED-3 (cell-death-abnormal ced-3 gene product), respectively; hCPP32 is human CPP32β.

FIG. 5 shows the kinetic analysis of apopain and a potent inhibitor using a fluorogenic substrate. a. Determination of $K_m$ for Ac-DEVD-AMC (structure in insert). b. Kinetics of inhibition of CPP32 by the peptide aldehyde Ac-DEVD-CHO. c. Comparison of PARP cleavage activity and inhibition by Ac-DEVD-CHO in THP-1 cell, osteosarcoma cell and chicken S/M extracts. METHODS. a. Ac-DEVD-AMC (inset) (AMC, amino-4-methylcoumarin) was prepared as follows: i) synthesis of N-Ac-Asp(OBn)-Glu(OBn)-Val-CO2H, ii) coupling with Asp(OBn)-7-amino-4-methylcoumarin, iii) removal of benzyl groups. Standard reaction mixtures (300 µl final volume), which contained the indicated concentrations of Ac-DEVD-AMC and 35 U of the purified PARP-cleavage apopain/CPP32 enzyme (1U=1 pmol AMC liberated per min at 25° C. at saturating substrate concentration) in 100 mM Hepes/KOH (pH 7.5), 10% (w/v) sucrose, 0.1% (w/v) CHAPS, 10 mM dithiothreitol, were incubated at 25° C. Reactions were monitored continuously in a spectrofluorometer at an excitation wavelength of 380 nm and an emission wavelength of 460 nm. Initial velocities and substrate concentrations were fit by nonlinear regression to the Michaelis-Menton equation (solid line). The results of several experiments indicated that the $K_m$ for cleavage of this substrate by apopain is 9.7±1.0. µM. b. Ac-DEVD-CHO was prepared as described for FIG. 2b. Reactions (300 µl) contained $1 \times K_m$ Ac-DEVD-AMC (10 µM) and the purified PARP-cleavage apopain enzyme (120 U) in the buffer described for panel a. Addition of the tetrapeptide aldehyde (50 nM) to this reaction mixture resulted in a time-dependent loss of enzyme activity (closed circles) whereas the reaction not containing inhibitor was strictly linear (open circles). The association rate constant ($k_{on}$) was calculated from several progress curves according to the equations developed by Morrison for analysis of slow and tight-binding inhibitors[43]. The complete inhibition of activity observed at infinite time with 50 nM Ac-DEVD-CHO indicates a $K_i$ of less than 1 nM for this inhibitor. c. Extracts from THP-1 cells, apoptotic osteosarcoma cells and chicken DU249 cells committed to apoptosis were prepared as described for FIG. 1b. The $K_m$ for cleavage of the synthetic fluorogenic tetrapeptide Ac-DEVD-AMC and the $k_{on}$ and $K_i$ values for the tetrapeptide aldehyde inhibitor Ac-DEVD-CHO were determined as described above for panels a and b, respectively.

FIG. 6 'shows in vitro apoptosis and selective inhibition by Ac-DEVD-CHO or by depletion of apopain-mediated PARP cleavage activity. a. Cytosols from progressively apoptotic osteosarcoma cells confer apoptotic changes upon healthy nuclei from non-apoptotic cells. The cytosol fraction from osteosarcoma cells at various stages of apoptotic death were incubated with isolated nuclei from non-apoptotic osteosarcoma cells and morphological changes were assessed by fluorescent microscopy after staining with Hoechst 33342. b. Attenuation of in vitro apoptosis by inhibition or depletion of apopain. Col. 2–9: The cytosol fraction from apoptotic osteosarcoma cells was combined with healthy nuclei from non-apoptotic osteosarcoma cells in the presence of varying concentrations of the CPP32 inhibitor Ac-DEVD-CHO (columns 3–8) or the ICE inhibitor Ac-YVAD-CHO (column 9). Col. 10–15: Pro-apoptotic osteosarcoma cell cytosols were depleted of PARP cleavage activity (columns 11–15) then incubated with healthy nuclei from non-apoptotic osteosarcoma cells in the presence of varying amounts of purified apopain (col. 12–14) or purified ICE (col. 15).

METHODS. Osteosarcoma cells at various stages of apoptosis and cytosolic extracts from them were prepared as described for FIG. 1. Nuclei were isolated from non-apoptotic (day 3) cells essentially as described before[36] except that the nuclear isolation buffer was 10 mM Pipes/KOH (pH 7.4), 10 mM KCl, 2 mM $MgCl_2$, 1 mM dithiothreitol, 10 µM cytochalasin B, 1 mM phenylmethylsulfonyl fluoride, 10 µg/ml pepstatin A, 20 µg/ml leupeptin, 10 µg/ml aprotinin. a. The isolated nuclei from $2\times10^6$ day-3 cells were combined with 25 µl of the cytosol fraction ($2.5\times10^6$ cell equivalents) from cells maintained for the indicated times in culture then incubated in 100 µl (final volume) of a mixture containing 10 mM Hepes/KOH (pH 7.0), 50 mM NaCl, 2 mM $MgCl_2$, 0.1 mM $CaCl_2$, 40 mM β-glycerophosphate, 1 mM dithiothreitol, 2 mM ATP, 10 mM creatine phosphate and 50 µg/ml creatine kinase. After 2 h at 37° C., nuclear chromatin was stained with 5 µg/ml Hoechst 33342 and examine by fluorescent microscopy (excitation wavelength 330 nm; emission wavelength 450 nm). Nuclei having brightly fluorescent, condensed and fragmented chromatin were scored as apoptotic whereas non-apoptotic nuclei were identified by weakly fluorescent, uniform chromatin staining. For each condition, a minimum of 250 nuclei in 5 separate fields were scored. Data are the average of two independent experiments. b. Col. 1–9: In vitro apoptosis was measured as described for panel a using nuclei from non-apoptotic, day 3 osteosarcoma cells (1–9) combined with the cytosol fraction from apoptotic, day 7 cells (2–9) in the presence of the indicated concentrations of Ac-DEVD-CHO (3–8) or Ac-YVAD-CHO (9). Data are the average of three independent experiments ± SEM.

Col. 10–15: PARP cleavage activity was depleted from the cytosol fraction of apoptotic, day 7 cells ($D7_{dep}$) by incubating 1 ml of the fraction with 100 nM Biotin-[X]-DEVD-CHO for 20 min then harvesting with 50 µl streptavidin-agarose (biotin binding capacity=63 nmol/ml). The depletion procedure was then repeated on the same fraction. In vitro apoptosis was measured as described for panel a using nuclei from non-apoptotic, day 3 osteosarcoma cells (10–15) combined with untreated day 7 cytosol (10) or depleted day 7 cytosol (11–15) supplemented with varying concentrations of purified apopain/CPP32 (12–15) or purified ICE (15). Lower concentrations of ICE also had no effect (not shown).

EXAMPLE 1

PARP Cleavage Activity in Progressively Apoptotic Osteosarcoma Cells

Figure 1B:
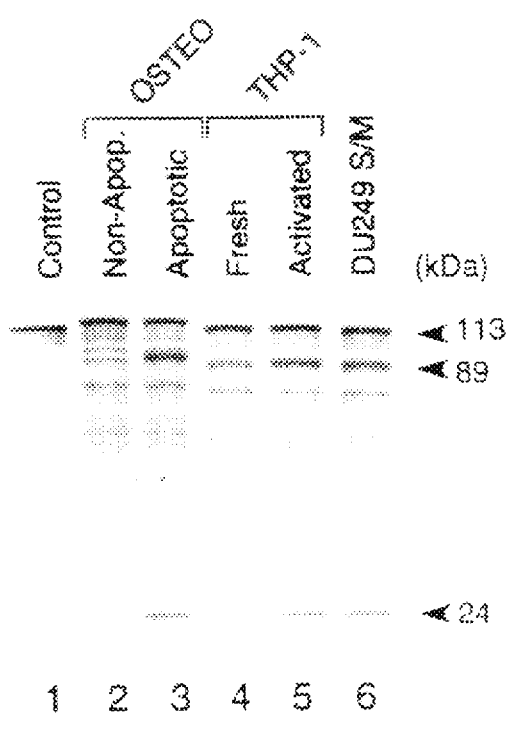
Figure 1C:
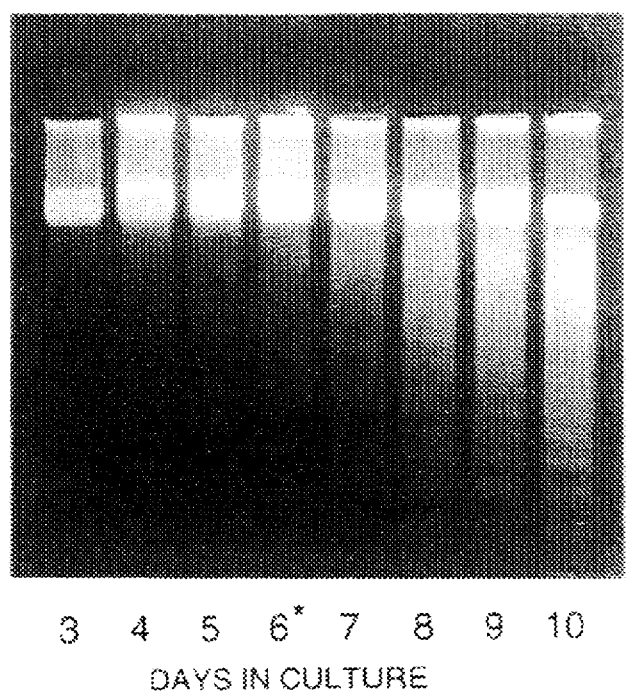
Figure 1D:
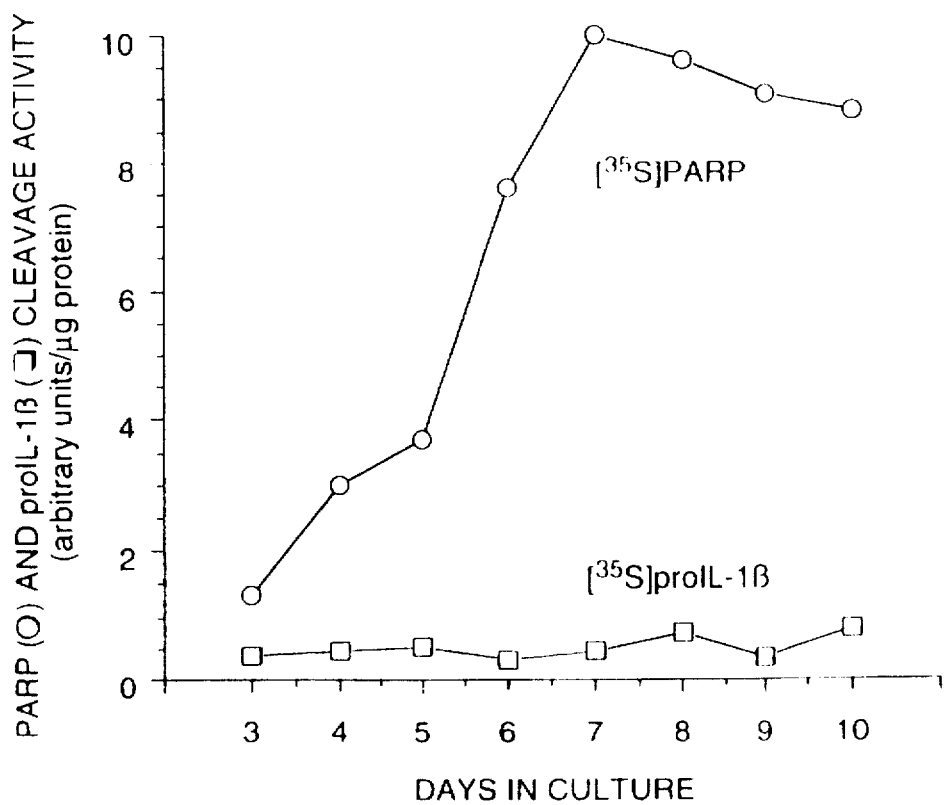

An early event that occurs concomitantly with the onset of apoptosis is the proteolytic breakdown of PARP by an unidentified protease with properties resembling those of ICE (prICE)[19]. The resulting cleavage (between $Asp^{216}$ and $Gly^{217}$) separates the amino-terminal DNA-nick sensor of PARP from its carboxy-terminal catalytic domain (FIG. 1a). In order to measure this proteolytic activity, [$^{35}$S]PARP was generated as a substrate by in vitro transcription/translation of a full-length human PARP cDNA clone and was then combined with various cell extracts (FIG. 1b). A human osteosarcoma cell line with a propensity for spontaneous apoptotic death contained substantial PARP cleavage activity that was markedly higher in extracts from apoptotic cells versus non-apoptotic cells (lane 2 vs 3). Osteosarcoma cells are a good model system for studying the events that occur during apoptosis. Upon reaching confluence in culture they undergo the morphological and biochemical changes characteristic of apoptotic death, including cell shrinkage, membrane blebbing, chromatin condensation and fragmentation (not shown) as well as internucleosomal DNA cleavage (FIG. 1c). Coincident with the progressive apoptosis that occurred in post-confluent osteosarcoma cell cultures, the PARP cleavage activity measured in cell extracts was elevated>10-fold (FIG. 1d). There was no detectable ICE in these extracts, as judged by immunoblotting, reverse-transcriptase PCR (not shown) and by the absence of proIL-1β processing, indicating that ICE is not necessary for apoptosis or for PARP cleavage. The lack of a role for ICE in apoptosis was confirmed in ICE-deficient mice where apoptosis occurred normally[29].

PARP cleavage activity was also measurable in cytoplasmic extracts of THP-1 cells, the human monocytic leukemia cell line from which ICE was originally purified, particularly after pre-incubation of the extracts at 37° C. (FIG. 1b, lane 4 vs 5). This suggests that the PARP cleavage enzyme requires activation of a latent form as has been described for ICE in this cell line[30]. PARP cleavage in apoptotic osteosarcoma cell extracts and activated THP-1 cell extracts was comparable to that in apoptotic chicken S/M extracts (lane 6) where this proteolytic activity was originally identified[19].

EXAMPLE 2

Inhibitors of PARP Cleavage

Figure 2B:
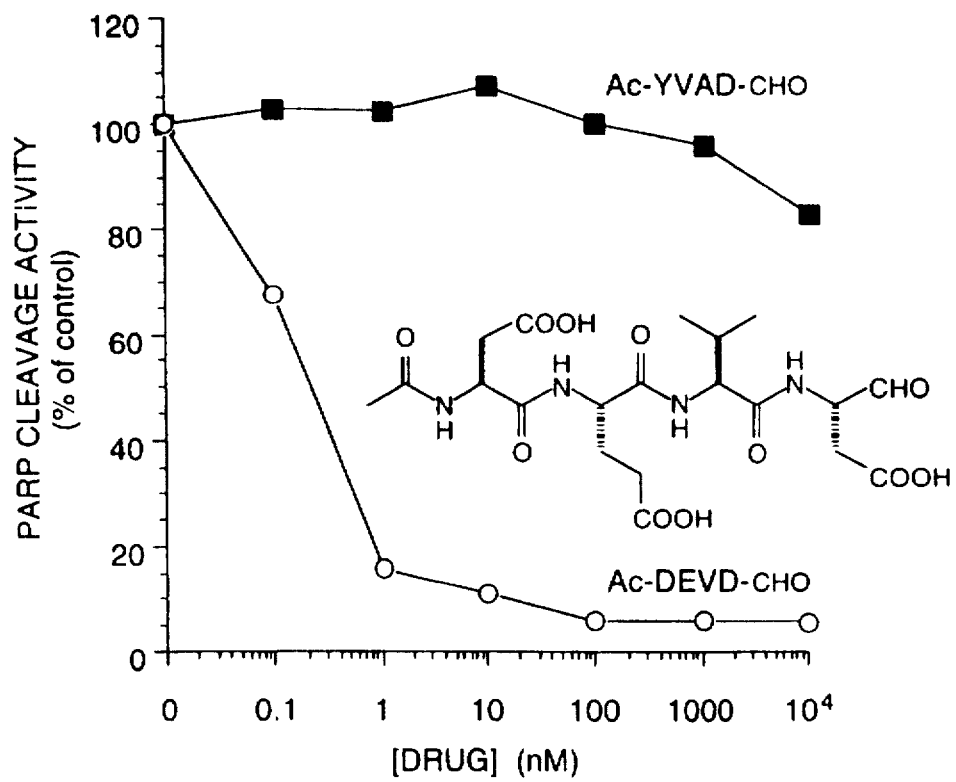
Figure 2A:
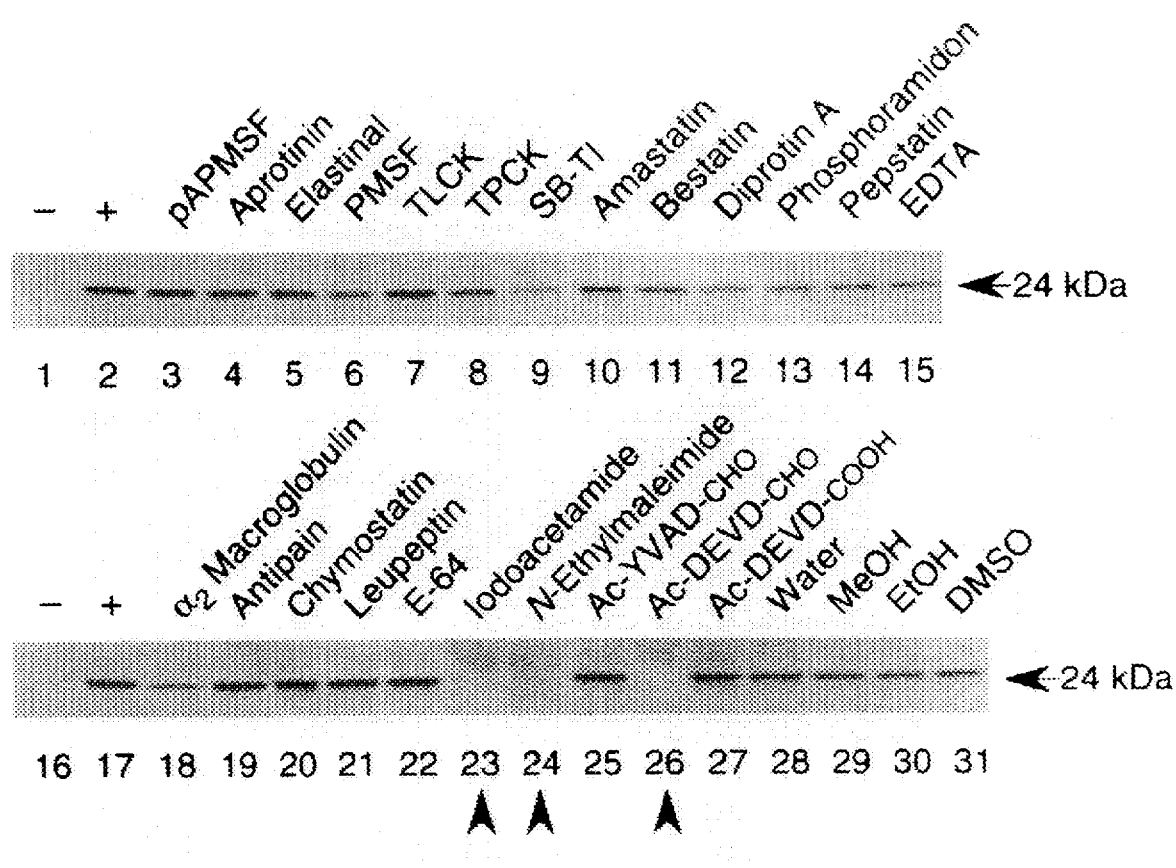

The proteolytic cleavage of PARP in cytosolic extracts from apoptotic osteosarcoma cells was abolished by the cysteine-alkylating reagents N-ethylmaleimide and iodoacetamide but not by E-64 (also a cysteine-protease inhibitor) or by inhibitors of serine-, aspartate- or metallo- proteases (FIG. 2a). This inhibitor profile is consistent with the PARP cleavage enzyme being a member of the emerging ICE-like family of cysteine proteases. In order to develop more potent and specific PARP cleavage inhibitors, the sequences proximal to the scissile bond were used as a template for inhibitor design. Appropriate peptide aldehydes can be potent inhibitors of cysteine proteases, as exemplified by the sensitivity of ICE to the tetrapeptide aldehyde Ac-YVAD-CHO ($K_i$= 0.76 nM). A tetrapeptide aldehyde containing the $P_1$-$P_4$ amino acid sequence of the PARP cleavage site ($DEVD^{216}$-$G^{217}$) was therefore synthesized and found to be a potent inhibitor of PARP breakdown (Ac-DEVD-CHO; FIG. 2b inset). Ac-DEVD-CHO inhibited the PARP cleavage activity in apoptotic osteosarcoma cell extracts with an $IC_{50}$ value of 0.2 nM. In contrast, the corresponding carboxylic acid (Ac-DEVD-COOH) and the tetrapeptide aldehyde containing the proIL-1β recognition sequence for ICE (Ac-YVAD-CHO) had $IC_{50}$ values>10 μM (FIGS. 2a & 2b). An identical inhibitor profile was found for the PARP cleavage activity in activated THP-1 cell extracts and in apoptotic chicken S/M extracts (not shown). The cowpox-virus serpin CrmA (the cytokine-response-modifier A (crmA) gene product), which is a potent inhibitor of $ICE^{31}$ ($K_i$<4 pM), had no inhibitory effect on PARP cleavage when tested up to 0.6 μM (not shown). PARP cleavage is therefore mediated by an E-64-insensitive cysteine protease that can be inhibited by low concentrations of the tetrapeptide aldehyde Ac-DEVD-CHO but not by high levels of potent inhibitors of ICE.

EXAMPLE 3
Purification of apopain, the PARP-Cleavage Protease

To identify the enzyme responsible for PARP inactivation in mammalian cells during apoptosis, it was purified to homogeneity from cultured human cells. PARP cleavage activity was highly elevated in osteosarcoma cells as they progressed into apoptosis upon reaching confluence; however, owing to the impracticality of obtaining sufficient quantities of an adherent cell line to purify the protease, THP-1 cells were used. Two lines of evidence suggested that the cysteine protease that cleaved PARP in THP-1 cells was the same as that in apoptotic osteosarcoma cells. First and most compelling, the kinetic parameters for catalysis and inhibition by Ac-DEVD-CHO were found to be virtually identical for the enzyme in extracts from both cell types (see below). Second, reverse-transcriptase PCR analysis indicated that with the exception of ICE (for which transcripts were detectable in THP-1 cells only), both THP-1 cells and apoptotic osteosarcoma cells contained transcripts for the same compliment of ICE/CED-3-like enzymes (namely; $ICE_{rel}$-II, ICH-1 and CPP32 but not $ICE_{rel}$-III) (not shown).

Figure 3A:
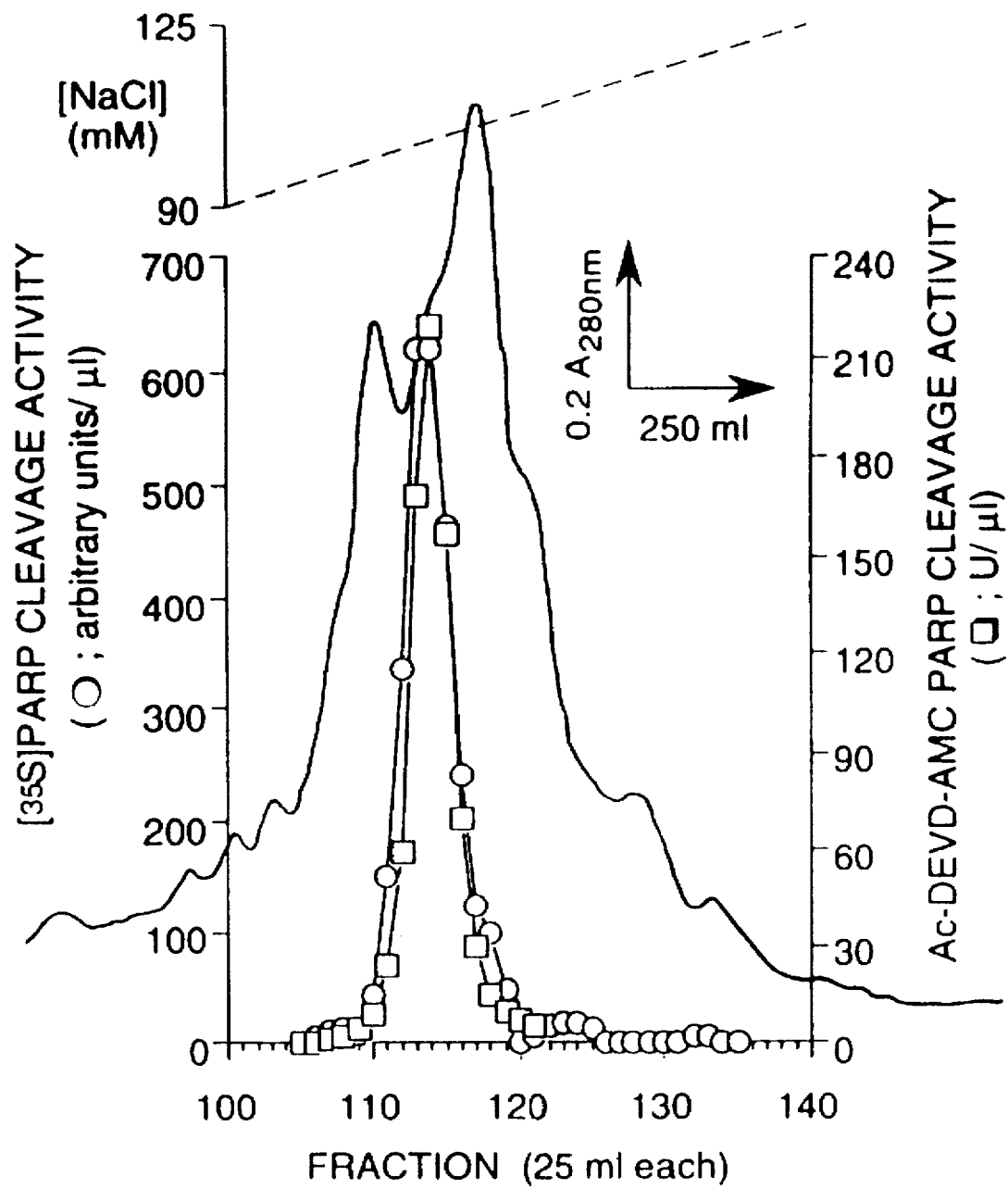
FIGS. 3a–c show purification of the PARP cleavage protease from THP-1 cells.
Figure 3B:
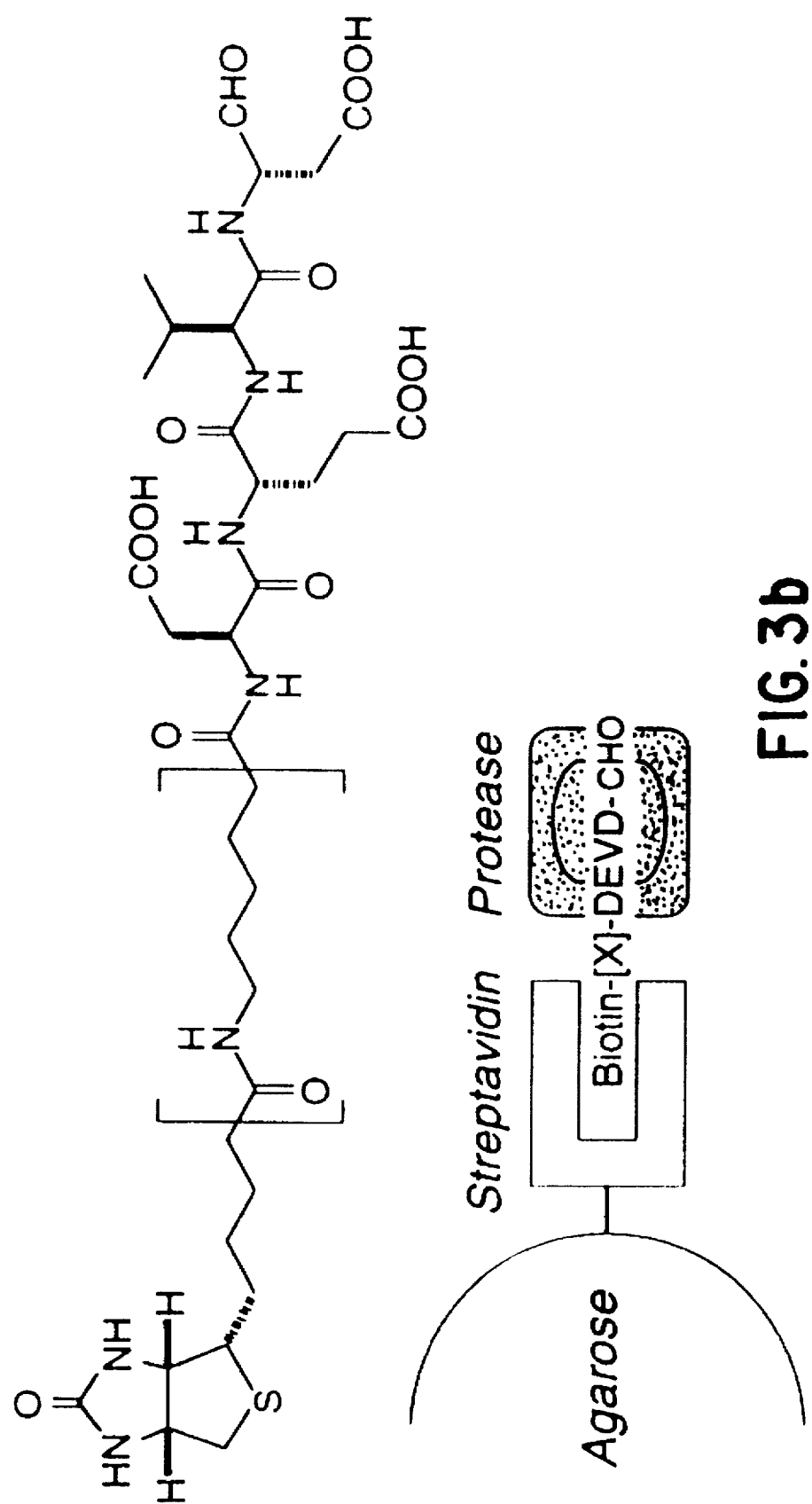
Figure 3C:
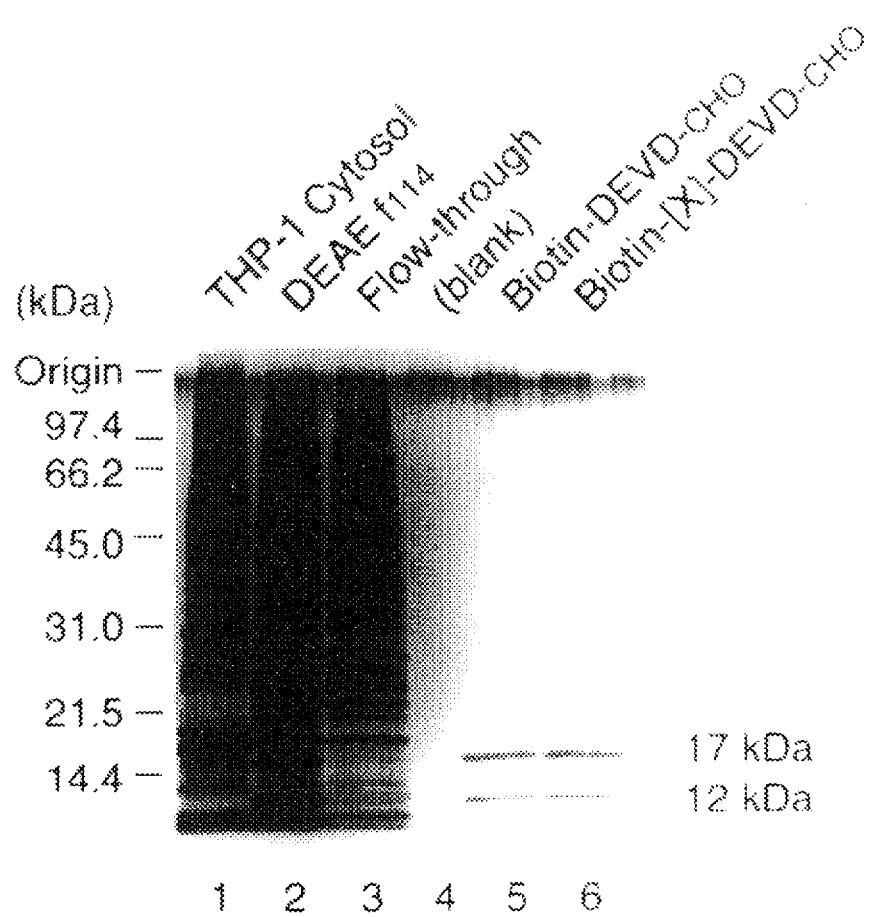

When cytosol fractions from THP-1 cells were resolved by DEAE anion-exchange chromatography, the PARP cleavage activity was separated from ICE immunoreactivity and proIL-1β cleavage activity which co-eluted from the column at a lower salt concentration (approximately 80 mM and 135 mM for ICE and PARP cleavage activities, respectively). The fractions containing PARP cleavage activity from several chromatographic runs were pooled and rechromatographed under identical conditions (FIG. 3a). In order to selectively purify this activity, two biotinylated derivatives of the Ac-DEVD-CHO tetrapeptide aldehyde inhibitor were synthesized as affinity ligands for the PARP cleavage enzyme (FIG. 3b). Biotinylated affinity ligands were used because they could be pre-incubated with the enzyme in order to overcome slow ligand binding (see below) by allowing full equilibrium to occur prior to harvesting. Both biotinylated tetrapeptide aldehydes had $IC_{50}$ values for inhibition of the PARP cleavage enzyme that were comparable to that of the non-biotinylated parent compound (0.2 nM; not shown). The DEAE-chromatography fraction at the peak of PARP cleavage activity was incubated with the biotinylated tetrapeptide aldehydes then harvested with streptavidin-agarose. After extensive washing, the purified PARP cleavage enzyme was eluted from the column with 2 mM biotin. SDS/polyacrylamide gel electrophoresis of the resulting samples indicated that the purified PARP cleavage enzyme was composed of two major polypeptides of approximately 17 and 12 kDa (FIG. 3c).

EXAMPLE 4
Structure of the PARP-Cleavage Protease: apopain/CPP32

Figure 4B:
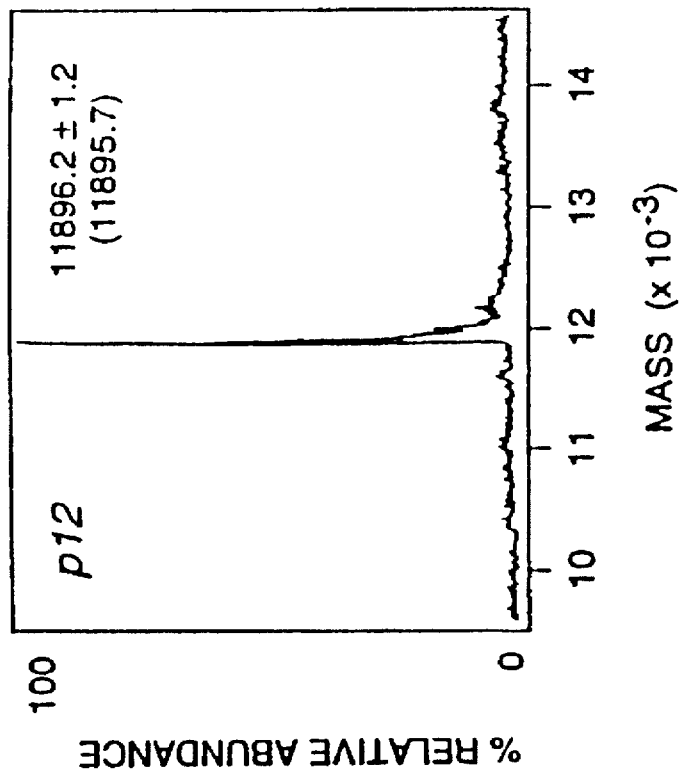
FIGS. 4a–e show the structure of PARP cleavage protease; apopain, which is derived from the inactive proenzyme CPP32.
Figure 4A:
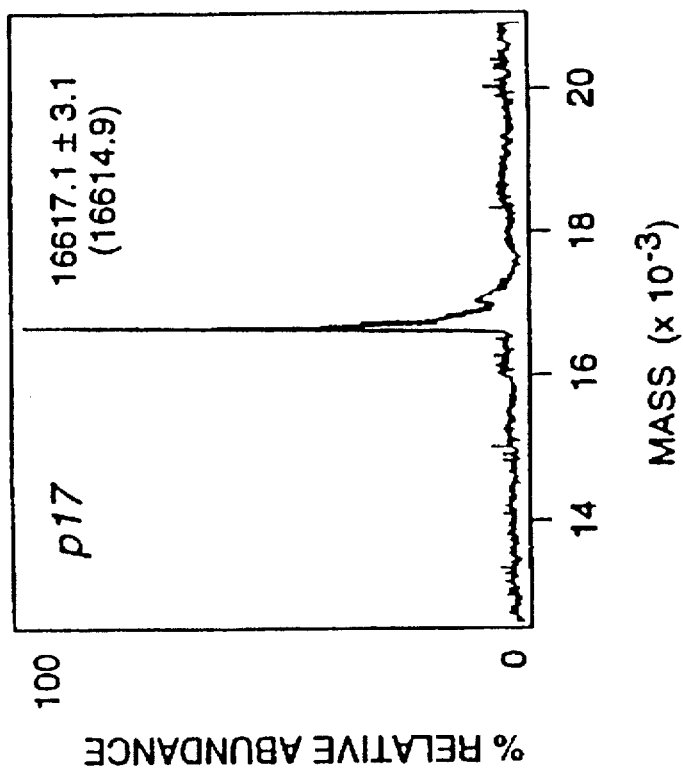

Electrospray mass spectroscopy analysis of the purified PARP cleavage enzyme indicated that the mass of the larger polypeptide was 16,617.1±3.1 and the smaller polypeptide was 11,896.2±1.2 (FIG. 4a). Amino-terminal sequence determination and tryptic maps of the purified apopain enzyme identified it as a protolytic product of the inactive CPP32 proenzyme, a member of the ICE/CED-3 family of cysteine proteases of unknown function that was recently cloned from Jurkat cells[25]. Cloned CPP32 was originally identified as two isoforms (CPP32a and CPP32β) which differ by a single conservative amino acid substitution ($Asp^{190}$ vs $Glu^{190}$ for CPP32a and CPP32β, respectively). The amino-terminal sequence of the 12 kDa subunit of the purified apopain PARP cleavage enzyme corresponded with CPP32β (FIG. 4b) as did the cDNA sequence of human CPP32 cloned from placenta, lung and kidney (not shown).

Figures 4C, 4D, 4E:
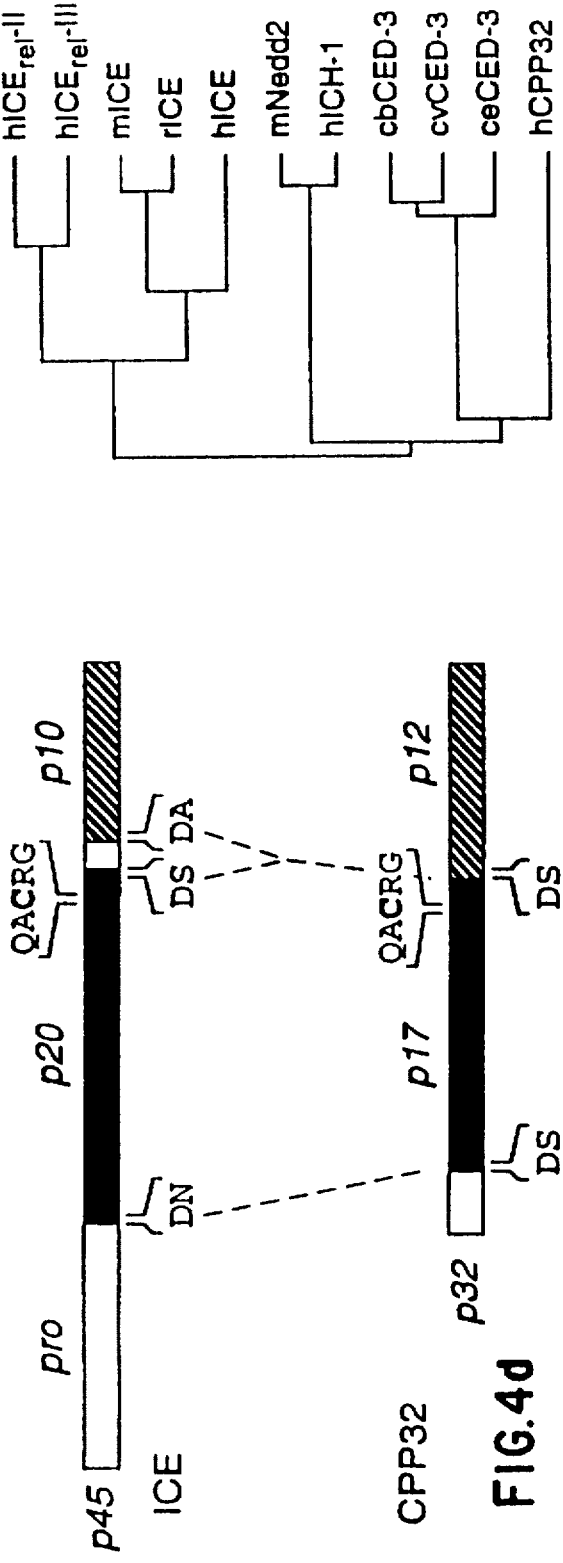

Both the mass determination and amino-terminal sequence of the two subunits were in agreement and demonstrated that both polypeptides were derived from the same 32 kDa CPP32 precursor polypeptide by cleavage between $Asp^{28}$-$Ser^{29}$ and $Asp^{175}$-$Ser^{176}$ (FIG. 4b). The organization of the CPP32 proenzyme is similar to that of ICE (FIG. 4c). Like ICE, the CPP32 proenzyme is composed of an amino-terminal prodomain followed by a larger subunit (p17), which contains the putative active site cysteine and histidine residues, that is then followed by the smaller subunit (p12). The major differences between ICE and CPP32 proenzymes are that a) the prodomain of CPP32 is substantially shorter, and b) there is no linker peptide separating the larger (p17) subunit of apopain from the smaller (p12) subunit in the CPP32 proenzyme. The presence of Asp residues in the P1 position of both the prodomain/p17 junction and the p17/p12 junction of CPP32 suggests that autocatalysis plays an important role in proenzyme activation as has been demonstrated for $ICE^{7,32,33}$.

Sequence alignment of all known members of the ICE/CED-3 family of cysteine proteases indicates that apopain/CPP32 is the most closely related of the mammalian enzymes to the pro-apoptotic nematode cell-death-abnormal ced-3 gene product (FIG. 4d). An alignment of the five known human enzymes in this family as well as CED-3 indicates that there is absolute conservation of the residues involved in catalysis as well as those involved in binding of the carboxylate side chain of the substrate P1 aspartic $acid^{33,34}$ (FIG. 4e). Conservation is also high near the Asp/Ser cleavage site at the carboxy terminus of the p20 subunit of ICE ($Asp^{296}$-$Ser^{297}$) and the p17 of CPP32 ($Asp^{175}$-$Ser^{176}$), suggesting that the active forms of the other members of this family are also heterodimers which are derived from proenzymes. Residues that might form the $P_2$-$P_4$ binding pockets, however, are not widely conserved, indicating that substrate specificity might be determined by one or more of these amino acids.

EXAMPLE 5
Kinetic Properties of Apopain and its Inhibitors

Figure 5A:
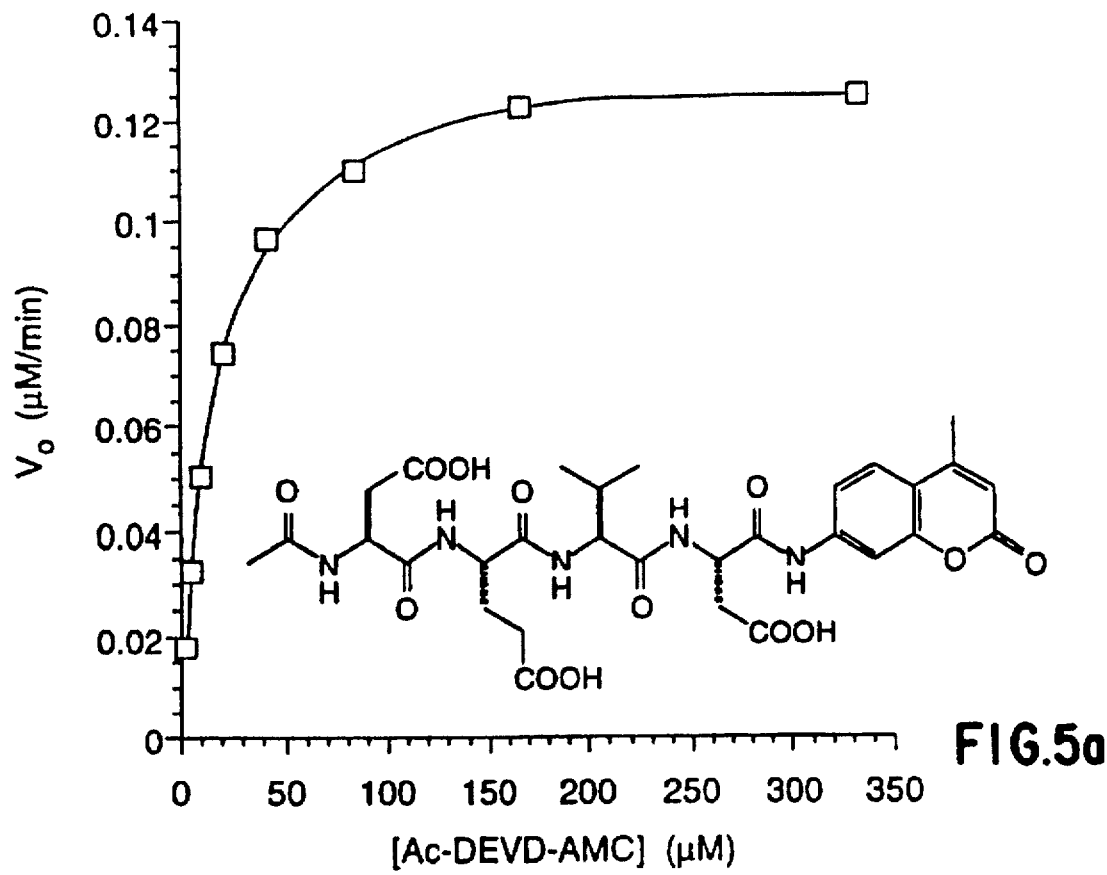

A continuous fluorometric assay for apopain was developed with the substrate Ac-DEVD-AMC (AMC, amino-4-methylcoumarin). The design of this substrate was based on the tetrapeptide-AMC motif that has been used successfully with $ICE^7$, except using the PARP cleavage site $P_1$-$P_4$ tetrapeptide (FIG. 5A inset). Cleavage of this substrate by apopain showed Michaelis-Menton kinetics with a $K_m$=9.7± 1.0 μM (FIG. 5a). This assay has facilitated a detailed investigation of the mechanism of inhibition of the enzyme by the tetrapeptide aldehyde Ac-DEVD-CHO.

Figure 5B:
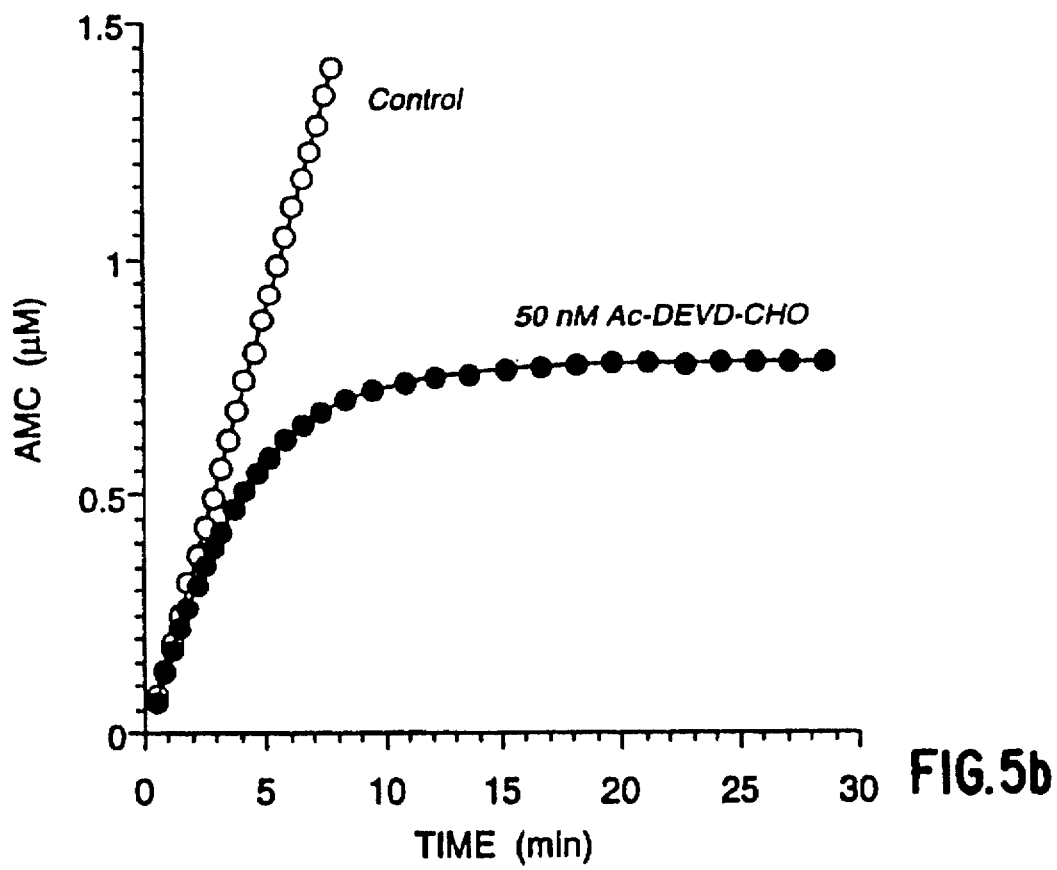

Peptide aldehydes are potent, reversible inhibitors of cysteine proteases that undergo nucleophilic addition of the catalytic cysteine to form a thiohemiacetal. Although the potency of aldehyde inhibitors was originally attributed to their ability to mimic the transition state in amide bond hydrolysis[35], the recently determined crystal structure of ICE with the tetrapeptide aldehyde Ac-YVAD-CHO clearly shows this inhibitor bound in a non-transition-state conformation, with the oxyanion of the thiohemiacetal being stabilized by the active site histidine[33]. The tetrapeptide aldehyde containing the appropriate recognition sequence for apopain, Ac-DEVD-CHO, is a potent, competitive inhibitor of this enzyme. It is slow binding, as shown by the time-dependent approach to equilibrium observed when enzyme was added to reaction mixtures containing inhibitor (50 nM) and 1×$K_m$ substrate (FIG. 5b). The solid line of FIG. 5b (closed circles) is theoretical for an association rate constant $k_{on}$=1.3×10$^5$M$^{-1}$s$^{-1}$. This rate constant, which is well below theoretical predictions of rates for diffusion-limited reactions (10$^8$–10$^{10}$M$^{-1}$s$^{-1}$), is similar to the corresponding rate constant for association of ICE with its tetrapeptide aldehyde inhibitor ($k_{on}$ Ac-YVAD-CHO=3.8×10$^5$M$^{-1}$s$^{-1}$). The nearly complete suppression of the activity that was seen at infinite time using 50 nM Ac-DEVD-CHO defines a $K_i$ for inhibition of apopain of<1 nM, making this among the most potent peptide aldehydes known for a cysteine protease.

In contrast to the potent inhibition of apopain observed with the tetrapeptide aldehyde Ac-DEVD-CHO, the ICE inhibitor Ac-YVAD-CHO ($K_i$ ICE=0.76 nM) was a very weak inhibitor of apopain ($K_i$ CPP32=12 µM), further evidence that these enzymes have distinct extended substrate specificities. This differential in potency can be attributed to the fact that residues implicated in binding the $P_4$ Tyr of proIL-1β, which is a key determinant for ICE, are not conserved in apopain/CPP32. The crystal structure of active ICE, for example, has indicated that the two key amino acids that interact with the $P_4$ Tyr of proIL-1β are His[342] and Pro[343] which are replaced by Asn and Ser, respectively, in both apopain/CPP32 and CED-3 (FIG. 4e). These latter residues in apopain/CPP32 would be better able to form the hydrogen bonds necessary to interact with the carboxylate side chain of the $P_4$ Asp of PARP. The enzymes also clearly have different macromolecular substrate specificities: purified ICE was unable to cleave PARP and purified apopain did not cleave proIL-1β at either the FEAD[27]-G[28] or DEVD[216]-G[217] cleavage sites (a 5000-fold excess of each enzyme was tested; not shown). The enzymes are also distinguished by their behaviour with the cowpox serpin, CrmA, which shows a more than 10,000-fold preference for ICE.

The catalytic and inhibitor constants for the PARP cleavage activity in extracts of THP-1 cells, apoptotic osteosarcoma cells, and apoptotic chicken S/M extracts were virtually identical (FIG. 5c), strongly suggesting that the same enzyme (apopain) cleaves PARP in all three cell types.

Figures 5C, 6A:
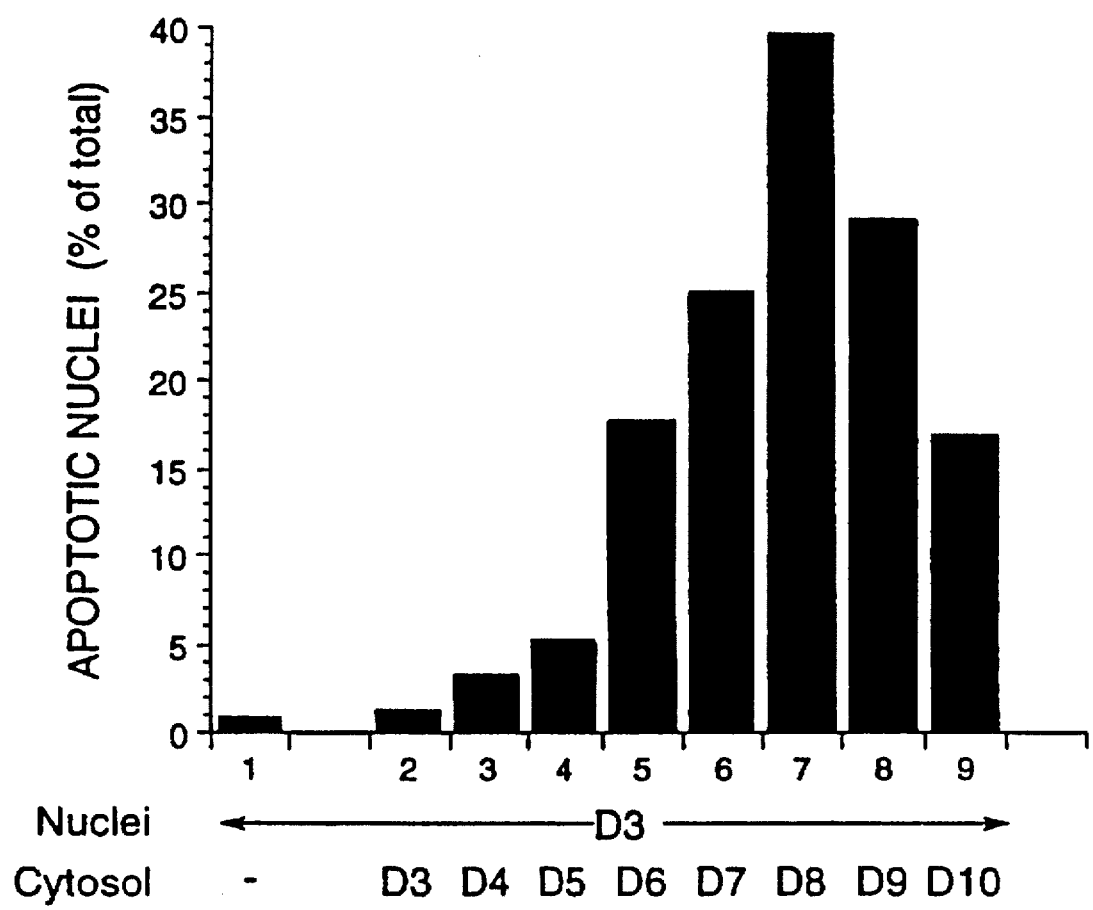

EXAMPLE 6
Attenuation of Apoptosis by Inhibitors of Apopain-Mediated PARP Cleavage Apoptotic events can be re-constituted in vitro. The isolated nuclei from healthy cells undergo the morphological changes that are characteristic of apoptosis (eg. chromatin condensation, fragmentation and margination as well as internucleosomal DNA cleavage) when they are incubated with the cytosol fraction from apoptotic cells[36]. Since the most potent and selective inhibitor of apopain-mediated PARP cleavage (Ac-DEVD-CHO) was membrane impermeable and hence inactive in intact cells, this system was established with human cells and used to study the effects of apopain inhibition or depletion on apoptosis in vitro. Cytosols from non-apoptotic osteosarcoma cells had little effect on nuclear morphology whereas those from progressively apoptotic cells were capable of inducing apoptosis-like changes in the recipient nuclei (FIG. 6a). The degree of apoptotic morphology conferred upon the otherwise healthy nuclei coincided with the degree of apoptosis occurring in the cells from which the cytosols were extracted (cf. FIG. 1c) as well as the level of PARP cleavage activity (cf. FIG. 1d).

If the PARP-cleaving apopain cysteine protease plays a key role in apoptosis, then inhibition or depletion of its activity should prevent these nuclear changes from occurring. Morphological changes that occurred when the cytosol fraction from apoptotic osteosarcoma cells was incubated with healthy nuclei from non-apoptotic cells could be attenuated by the tetrapeptide aldehyde inhibitor of apopain-mediated PARP cleavage, Ac-DEVD-CHO (IC$_{50}$=10–100 nM), but not with the ICE inhibitor, Ac-YVAD-CHO (FIG. 6b; columns 2–9). Similarly, if apopain/CPP32 was depleted from the cytosol fraction of apoptotic osteosarcoma cells using the biotinylated affinity ligand, these PARP cleavage-deficient extracts were largely incapable of conferring apoptotic changes to healthy recipient nuclei. The pro-apoptotic capabilities of depleted extracts was restored when they were supplemented with purified apopain/CPP32 but not when they were supplemented with purified ICE (columns 10–15). Together, these experiments suggest that apopain initiates key events in apoptosis and that inhibition or depletion of its activity prevents apoptosis from occurring.

EXAMPLE 7
Expression Of The Apoptain Polypeptide By In Vitro Transcription/Translation And By Transfection Into Host Cells Vectors containing the apopain encoding DNA sequence are used to drive the translation of the apopain polypeptide in rabbit reticulocyte lysates, mammalian host cells, and in baculovirus infected insect cells. The experimental procedures are essentially those outlined in the manufacturers' instructions.

a) In vitro Transcription/Translation pBluescript II SK+:apopain plasmid DNA (with apopain in the T7 orientation) is linearized by Bam HI digestion downstream of the apopain insert. The linearized plasmid is purified and used as a template for run-off transcription using T7 RNA polymerase in the presence of m7G(5')ppp (5')G. The resulting capped apopain transcripts are purified by lithium chloride precipitation and used to drive the translation of apopain in nuclease-pretreated rabbit reticulocyte lysate in the presence of L-[$^{35}$S]methionine.

b) Expression in Mammalian Cells

The apopain protein is expressed in mammalian host cells following transfection with either pcDNA I/Amp:apopain (under control of the CMV promoter) or pSZ9016-1:apopain (under control of the HIV LTR promoter). In the latter case (pSZ9016-1:apopain), cells are co-transfected with the TAT expressing plasmid pSZ90161 :TAT. For both apopain expression plasmids, COS-7 cells are transfected using either DEAE-dextran or lipofection with Lipofectamine (BRL).

c) Expression in Insect Cells

The apopain—containing baculovirus transfer vector pVL1393:T7 apopain HA is used to produce recombinant baculovirus (*Autographa californica*) by in vivo homologous recombination. Epitope tagged apopain is then expressed in Sf9 (*Spodoptera frugiperda*) insect cells grown in suspension culture following infection with the apopain-containing recombinant baculovirus.

EXAMPLE 8

Cloning Of Of Apoptain For Expression Of The Apoptain Polypeptide In Other Host Cell Systems a) Cloning of apoptain cDNA into a bacterial expression vector.

Recombinant apopain is produced in a bacterium such as *E. coli* following the insertion of the optimal apopain cDNA sequence into expression vectors designed to direct the expression of heterologous proteins. These vectors are constructed such that recombinant apopain is synthesized alone or as a fusion protein for subsequent manipulation. Expression may be controlled such that recombinant apopain is recovered as a soluble protein or within insoluble inclusion bodies. Vectors such as pBR322, pSKF, pUR, pATH, pGEX, pT7-5, pT7-6, pT7-7, pET, pIBI (IBI), pSP6/T7-19 (Gibco/BRL), pBluescript II (Stratagene), pTZ18R, pTZ19R (USB), pSE420 (Invitrogen) or the like are suitable for these purposes.

b) Cloning of apopain cDNA into a yeast expression vector

Recombinant apopain is produced in a yeast such as *Saccharomyces cerevisiae* following the insertion of the optimal apopain cDNA cistron into expression vectors designed to direct the intracellular or extracellular expression of heterologous proteins. In the case of intracellular expression, vectors such as EmBLyex4 or the like are ligated to the apopain cistron [Rinas, U. et al., Biotechnology 8: 543–545 (1990); Horowitz B. et al., J. Biol. Chem. 265: 4189–4192 (1989)]. For extracellular expression, the apopain cistron is ligated into yeast expression vectors which fuse a secretion signal (a yeast or mammalian peptide) to the amino terminus of the apopain protein [Jacobson, M. A., Gene 85: 511–516 (1989); Riett L. and Bellon N. Biochem. 28: 2941–2949 (1989)].

c) Cloning of apopain cDNA into a viral expression vector

Recombinant apopain is produced in mammalian host cells, such as HeLa S3 cells, after infection with vaccinia virus containing the apopain cDNA sequence. To produce apopain:vaccinia virus, the apopain cDNA is first ligated into a transfer vector, such as pSC 11, pTKgptF1s, pMJ601 or other suitable vector, then transferred to vaccinia virus by homologous recombination. After plaque purification and virus amplification, apopain:vaccinia virus is used to infect mammalian host cells and produce recombinant apopain protein.

EXAMPLE 9

Process for the production of apopain polypeptide

Recombinant apopain is produced by a) transforming a host cell with DNA encoding apopain protein to produce a recombinant host cell;

b) culturing the recombinant host cell under conditions which allow the production of apopain; and c) recovering the apopain.

The recombinant apopain is purified and characterized by standard methods.

EXAMPLE 10

Compounds that modulate apopain activity may be detected by a variety of methods. A method of identifying compounds that affect apopain comprises:

(a) mixing a test compound with a solution containing apopain to form a mixture;

(b) measuring apopain activity in the mixture; and (c) comparing the apopain activity of the mixture to a standard.

Compounds that modulate apopain activity may be formulated into pharmaceutical compositions. Such pharmaceutical compositions may be useful for treating diseases or conditions that are characterized by altered apopain activity. Examples of diseases wherein the apopain activity is increased include immune deficiency syndromes, pathogenic infections, cardiovascular and neurological injury, alopecia, aging, Parkinson's disease and Alzheimers disease. For these diseases, therapeutic treatment comprises treatment with compounds that decrease the apopain activity. Examples of diseases wherein the apopain activity is decreased include autoimmune diseases, leukemias, lymphomas and other cancers. For these diseases, therapeutic treatment comprises treatment with compounds that increase apopain activity.

EXAMPLE 11

N-Acetyl-aspartyl-glutamyl-valinyl-aspartic acid

Step 1

N-t-BOC-L-Aspartic acid dibenzyl ester

To a mixture of N-t-BOC-L-aspartic acid benzyl ester (4.00 g, 12.3 mmol), benzyl alcohol (1.46 g, 13.5 mmol) and HOBt (2.16 g, 16.0 mmol) in 24 mL of $CHCl_3$ and 2 mL of DMF cooled to 0° C. was added EDCI (3.54 g, 18.4 mmol). After stirring 3 h 30 min at 5° C. it was poured in $H_2O$ (25 mL) and the organic phase separated, washed once with $H_{2O}$ (10 mL), dried over $Na_2SO_4$ and the solvent removed. Chromatography on silica gel (eluted with 10% EtOAc in Hexane) afforded 2.10 g (41 %) of the title compound.

$^1$H NMR ($CDCl_3$, 400 MHz) $\delta$1.41 (s, 9H), 2.95 (AB, 2H), 4.62 (m, 1H), 5.05 (s, 2H), 5.11 (s, 2H), 5.49 (d, 1H), and 7.32 (m, 10H).

Step 2

L-Aspartic acid dibenzyl ester

The N-t-Boc (0.300 g, 0.72 mmol) of Step 1, Example 11 in 1.5 mL of $CHCl_3$ was added to a saturated solution of HBr in 2.7 mL $CHCl_3$ & 0.3 mL MeOH at -78° C. The solution was brought to -20° C., left 15 min and poured into saturated $NaHCO_3$. The organic phase was separated. The aqueous phase was extracted with $CH_2Cl_2$ (10 mL) and the organic phases combined and dried over $Na_2SO_4$. The solvent was removed to yield 0.212 g (93%) of the crude title compound.

$^1$H NMR ($CDCl_3$, 400 MHz) $\delta$2.7–3.0 (m, 4H), 3.95 (dd, 1H), 5.05 (s, 2H), 5.10 (s, 2H) and 7.3 (s, 10H).

Step 3

N-Ac-Asp-(Bz)-Glu(Bz)-Val-Asp(di-bz)

To a mixture of the amine (0.043 g, 0.13 mmol) of Step 2, Example 11, acid (0.074 g, 0.12 mmol) of Step 6, Example 12 and HOBt (0.021 g, 0.15 mmol) in 0.5 mL of $CHCl_3$ at 0° C. was added EDCI (0.034 g, 0.18 mmol). Similar workup to that in Step 1 of Example 11 afforded 0.105 g (94%) of the title compound after chromatography on silica gel (eluted with 5% MeOH in $CHCl_3$).

$^1$H NMR ($CDCl_3$, 400 MHz) $\delta$0.85 (dd, 6H), 1.98 (s, 3H), 2.0–2.2 (m, 3H), 2.4–2.5 (m, 2H), 2.7–2.9 (m, 2H), 3.0–3.1 (m, 2H), 4.23 (dd, 1H), 4.33 (m, 1H), 4.75 (m, 1H), 4.85 (m, 1H), 5.0–5.1 (m, 8H), 6.62 (d, 1H), 6.86 (m, 2H), 7.30 (m, 20H) and 7.47 (d, 1H).

Step 4

N-Ac-Asp-Glu-Val-Asp

The protected tetrapeptide (24 mg) of Step 3 of Example 11 in 1.5 mL HOAc and 0.5 mL MeOH and 20 mg of Pd—C (5%) were treated with H$_2$ for 2h. The mixture was filtered and the solvent removed. The crude was dissolved in H$_2$O and lyophilized to give 13 mg (93%) of the title compound.

$^1$H NMR (DMSO-d6—CDCl3, 400 MHz) d 0.82 (dd, 6H), 1.77 (m, 1H), 1.85 (s, 3H), 2.0 (m, 2H), 2.2 (m, 2H), 2.5–2.7 (m, 4H), 4.15 (dd, 1H), 4.39 (m, 1H), 4.52 (m, 2H), 7.57 (d, 1H), 7.88 (m, 2H) and 8.05 (d, 1H).

FAB HRMS calculated for C$_{20}$H$_{31}$N$_4$O$_{12}$=519.19385 Found=519.19383

EXAMPLE 12

Step 1

N-(tert-Butyloxycarbonyl)-L-valine allyl ester

To a solution of N-(tert-butyloxycarbonyl)-L-valine (10.53 g; 48.5 mmol) and allyl alcohol (33 mL; 49 mmol) in 150 mL CHCl$_3$ at 0° C. was added HOBt (8.53 g; 63.1 mmol) then EDCI (13.88 g, 72.4 mmol). The final mixture was stirred at 4° C. for 12 h then poured in to 100 mL NH$_4$OAc (25%). The organic phase was separated. The aqueous phase was washed with 50 mL of CHCl$_3$. The organic phases were combined, dried over Na$_2$SO$_4$, concentrated and flash chromatographed on silica gel (hexane/ EtOAc 9:1) to yield 5.10 g (41 %) of the title compound.

$^1$H NMR (400 MHz, CDCl$_3$) δ5.89 (m, 1H), 5.31 (d, 1H), 5.22 (d, 1H), 4.99 (d, NH), 4.60 (m, 2H), 4.22 (m, 1H), 2.13 (m, 1H), 1.44 (s, 9H), 0.96 (d, 3H), 0.87 (d, 3H).

Step 2

L-Valine allyl ester

A solution of 100 mL CHCl$_3$/10% MeOH saturated at −20° C. with HBr gas was cooled to −78° C. To this solution was added N-(tert-Butyloxycarbonyl)-L-valine allyl ester (5.10 g, 19.8 mmol) dissolved in 10 mL CHCl$_3$. The mixture was warmed to −20° C., stirred 15 min then poured into ice cold saturated NaHCO$_3$ (300 mL). The organic phase was separated. The aqueous phase was washed with 50 mL of CHCl$_3$. The organic phases were combined, dried over Na$_2$SO$_4$, concentrated to afford 3.10 g (99%) of the title compound which was used without further purification.

$^1$H NMR (400 MHz, CDCl$_3$) δ5.91–5.87 (m, 1H), 5.32 (dq, 1H), 5.22 (dq, 1H), 4.61–4.68 (m, 2H), 3.30 (d, 1H) 2.02 (m, 1H), 0.96 (d, 3H), 0.88 (d, 3H).

Step 3

N-(tert-Butyloxycarbonyl)-L-glutamyl-g-benzyl ester-L-valine allyl ester

To a solution of N-(tert-butyloxycarbonyl)-L-glutamyl-g-benzyl ester (8.02 g, 23.8 mmol) and L-valine allyl ester (3.10 g, 19.7 mmol) in 60 mL CHCl$_3$ at 0° C. was added HOBt (4.17 g, 30.9 mmol) then EDCI (6.85 g, 35.7 mmol). The final mixture was stirred at 4° C. for 12 h then poured into 100 mL of aqueous NH$_4$OAc (5%). The organic phase was separated, washed with 100 mL of saturated NaHCO$_3$, dried over Na$_2$SO$_4$, concentrated and flash chromatographed on silica gel (hexane/EtOAc 4:1) to yield 6.36 g (68%) of the title compound.

$^1$H NMR (400 MHz, CDCl$_3$) δ7.36–7.28 (m, 5H), 6.76 (d, NH), 5.92–5.82 (m, 1H), 5.30 (dq, 1H), 5.22 (dq, 1H), 5.11 (s, 2H), 4.65–4.55 (m, 2H), 4.50 (dd, 1H), 4.19 (d, NH), 2.57–2.46 (m, 2H), 2.21–2.04 (m, 2H), 1.97–1.88 (m, 1H), 1.41 (s, 9H), 0.92 (d, 3H), 0.89 (d, 3H).

Step 4

L-Glutamyl-g-benzyl ester-L-valine allyl ester

A solution of 200 mL CHCl$_3$/10% MeOH saturated at −20° C. with HBr gas was cooled to −78° C. To this solution was added N-(tert-Butyloxycarbonyl)-L-glutamyl-g-benzyl ester L-valine allyl ester (6.36 g, 13.3 mmol) dissolved in 20 mL CHCl$_3$. The mixture was warmed to −20° C., stirred 15 min then poured in ice cold saturated NaHCO$_3$ (500 mL). The organic phase was separated. The aqueous phase was washed with 100 mL of CHCl$_3$. The organic phases were combined, dried over Na$_2$SO$_4$, and concentrated to afford 5.00 g (99%) of the title compound and was used without further purification.

$^1$H NMR (400 MHz, CDCl$_3$) δ7.67 (d, NH), 7.36–7.28 (m, 5H), 5.93–5.84 (m, 1H), 5.31 (dq, 2H), 5.22 (dq, 2H), 5.11 (s, 2H), 4.68–4.56 (m, 2H), 4.50 (dd, 1H), 3.5 (d, NH2), 2.52 (t, 2H), 2.21–2.10 (m, 2H), 1.94–1.89 (m, 1H), 0.93 (d, 3H), 0.88 (d, 3H).

Step 5

N-(tert-Butyloxycarbonyl)-L-aspartyl-b-benzyl ester-L-glutamyl-b-benzyl ester-L-valine allyl ester To a solution of L-glutamyl-g-benzyl ester-L-valine allyl ester (5.00 g, 13.3 mmol) and N-(tert-butyloxycarbonyl)-L-aspartyl-β-benzyl ester (5.23 g, 16.2 mmol) in 50 mL CHCl$_3$ at 0° C. was added HOBt (4.17 g, 30.9 mmol) then EDCI (6.85 g, 35.7 mmol). The final mixture was stirred at 4° C. for 5 h then poured in 100 mL of aqueous NH$_4$OAc (5%). The organic phase was separated, washed with 100 mL of saturated NaHCO$_3$, dried over Na$_2$SO$_4$, concentrated and flash chromatographed on silica gel (CHCl$_3$/MeOH 2%) to yield 8.84 g (98%) of the title compound.

$^1$H NMR (400 MHz, CDCl$_3$) δ7.35–7.24 (m, 11H), 6.84 (d, NH), 5.92–5.82 (m, 1H), 5.54 (d, NH), 5.30 (dq, 1H), 5.22 (dq, 1H), 5.12 (dd, 2H), 5.06 (dd, 2H), 4.64–4.54 (m, 2H), 4.51–4.45 (m, 2H), 3.04 (dd, 1H), 2.73 (dd, 1H), 2.60–2.43 (m, 2H), 2.22–2.12 (m, 2H), 2.01–1.92 (m, 1H), 1.42 (s, 9H), 0.91 (d, 3H), 0.88 (d, 3H).

Step 6

N-Acetyl-L-(β-benzylaspartyl)-L-(g-benzylglutamyl)-L-valine

To a 0° suspension of N-acetyl -L-(β-benzylaspartyl)-L-(g-benzylglutamyl-L-valine allyl ester(0.530 g, 0.84 mmol) and tetrakis(triphenylphosphine) palladium (0.92 g, 0.08 mmol) in 6 ml DMF was added pyrrolidine (0.072 ml, 0.86 mmol) dropwise. After 25 min, EtOAc (40 ml) and NH$_4$OAc 25% (20 ml) were added. The organic phase was separated and the aqueous phase extracted with more EtOAc (20 ml). The organic phases were combined, dried over Na$_2$SO$_4$, concentrated and flash chromatographed in silica gel (CHCl$_3$/MeOH/HOAc, 95/4.5/0.5) to yield 0.42 g (86%) of the title compound.

$^1$H NMR (400 MHz, CDCl$_3$) δ0.92 (6H, t, J=6.2Hz), 1.99 (3H, s), 2.03 (1H, m), 2.1–2.2 (2H, m), 2.50 (2H, m), 2.70–3.00 (2H, AB), 4.39 (1H, dd, J=5.30, J=8.2 Hz), 4.48 (1H, m), 4.80 (1H,m), 5.06 (2H, s), 5.10 (2H, s), 6.84 (1H, m) 7.09 (1H, d, J=7.7Hz), 7.30 (10 H, m) and 7.61 (1H, d, J=7.2 Hz).

Step 7

N-(N-Acetyl-L-aspartyl-β-benzyl ester-L-glutamyl-g-benzyl ester-L-valine)-4-amino-5-benzyloxy-2-oxotetrahydrofuran To a solution of N-acetyl-L-(β-benzylaspartyl)-L-(g-benzylglutamyl)-L-valine (608 mg, 1.04 mmol) and N-allyloxycarbonyl-4-amino-5-benzyloxy-2-oxotetrahydrofuran (335 mg, 1.15 mmol) in 5 mL CHCl$_3$ and 0.7 mL DMF was added PdCl$_2$(PPh$_3$)$_2$ (43 mg, .060 mmol) then Bu$_3$SnH (310 mL, 1.15 mmol). The mixture was stirred 10 min and CO$_2$ evolution was observed. An extra amount of Bu$_3$SnH (310 mL, 1.15 mmol) was added then the solution was cooled to 0° C. HOBt (284 mg, 2.10 mmol) then EDCI (245 mg, 1.28 mmol) were added. The final mixture was stirred at 0° C. for 4 h then diluted with 100 mL CHCl$_3$, poured into 20 mL NH$_4$OAc (25%). The organic phase was separated, washed with 20 mL of saturated NaHCO$_3$, dried over Na$_2$SO$_4$, concentrated and flash chromatographed on silica gel (CHCl$_3$/MeOH 5%) to yield 790 mg (98%) of the title compound as a mixture (1:1) of diastereoisomers.

$^1$H NMR (400 MHz, CDCl$_3$) δ8.22 (d, NH), 7.73 (d, NH), 7.37–7.25 (m, 15H), 6.98–6.82 (m, NH), 6.52 (d, NH), 5.58 (s), 5.48 (d), 5.12–5.00 (m), 4.86 (d), 4.79 (d), 4.74–4.59 (m), 4.52 (dd), 4.31–4.24 (m), 4.17 (dd), 3.07 (dd), 2.94 (dd), 2.91–2.85 (m), 2.77 (dd), 2.74–2.38 (m), 2.28–2.23 (m), 2.16–2.01 (m), 2.07 (s, CH3CONH), 1.99 (s, CH$_3$CONH), 0.89–0.8 (m).

Step 8

N-(N-Acetyl-L-aspartyl-L-glutamyl-L-valinyl)-3-amino-3-formylpropionic acid

To as suspension of the product of step 7 (51 mg, 66 mmol) in 5 mL MeOH was added 50 mg of Pd(OH)$_2$(20% on carbon).

The mixture was stirred under an atmosphere of H$_2$ for 24 h. The catalyst was filtered on celite, washed with 10 mL MeOH. The MeOH extract was concentrated and flash chromatographed on silica gel (CHCl$_3$/MeOH 5%) to afford, after lyophilizing the residue from 5 mL H$_2$O &10 mL AcOH, 17 mg (47%) of the title compound.

$^1$H NMR (400 MHz, CD$_3$OD) δ4.67 (t, 1H), 4.55 (dd, 1H), 4.40–4.35 (m, 1H), 4.31–4.24 (m, 1H), 4.09–4.15 (m, 1H), 2.85 (dd, 1H), 2.71 (dd, 1H), 2.70–2.60 (m, 1H), 2.54–2.46 (m, 1H), 2.43–2.38 (m, 2H), 2.19–2.04 (m, 2H), 1.99 (s, 3H), 1.97–1.91 (m, 1H), 0.95 (d, 3H), 0.93 (d, 3H), HRMS FAB m/e calc'd for C$_{20}$H$_{30}$N$_4$O$_{11}$+H$^+$: 503.19889, found 503.19893.

References for this work include the following:
1. Kerr, J. F., Wyllie, A. H. and Currie, A. R. Br. J. Cancer 26, 239–257 (1972).
2. Martin, S. J., Green, D. R. and Cotter, T. G. Trends Biochem. Sci. 19, 26–30 (1994).
3. Barr, P. J. and Tomei, L. D. Biotechnology 12, 487–493 (1994).
4. Carson, D. A. and Ribeiro, J. M. Lancet 341, 1251–1254 (1994).
5. Ellis, R. E., Yuan, J. and Horvitz, H. R. Annu.Rev.Cell-.Biol. 7, 663–698 (1991).
6. Yuan, J., Shaham, S., Ledoux, S., Ellis, J. M. and Horvitz, J. R. Cell 75, 641–652 (1993).
7. Thornberry, N. A., Bull, H. G., Calaycay, J. R., Chapman, K. T., Howard, A. D., Kostura, M. J., Miller, D. K., Molineaux, S. M., Weidner, J. R., Aunins, J., Elliston, K. O., Ayala, J. M., Casano, F. J., Chin, J., Ding, G. J.-F., Egger, L. A., Gaffney, E. P., Limjuco, G., Palyha, O. C., Raju, S. M., Rolando, A. M., Salley, J. P., Yamin, T.-T., Lee, T. D., Shively, J. E., MacCross, M., Mumford, R. A., Schmidt, J. A. and Tocci, M. J. Nature 356, 768–774 (1992).
8. Cerretti, D. P., Kozlosky, C. J., Mosley, B., Nelson, N., Van Ness, K., Greenstreet, T. A., March, C. J., Kronheim, S. R., Druck, T., Cannizzaro, L. A., Huebner, K. and Black, R. A. Science 256, 97–100 (1992).
9. Miura, M., Zhu, H., Rotello, R., Hartwieg, E. A. and Yuan, J. Cell 78, 653–660 (1993).
10. Gagliardini, V., Fernandez, P.-A., Lee, R. K. K., Drexier, H. C. A., Rotello, R. J., Fishman, M. C. and Yuan, J. Science 263, 826–828 (1994).
11. Juarez-Salinas, H., Sims, J. L. and Jacobson, M. K. Nature 282, 740–741 (1979).
12. Berger, N. A., Sikorski, G. W., Petzold, S. J. and Kurohara, K. K. Biochemistry 19, 289–293 (1980).
13. Satoh, M. S. and Lindahl, T. Nature 356, 356–358 (1992).
14. Ding, R., Pommier, Y., Kang, V. H. and Smulson, M. J. Biol. Chem. 267, 12804–12812 (1992).
15. Smulson, M., Istock, N., Ding, R. and Cherney, B.Biochemistry 33, 6186–6194 (1994).
16. Ding, R. and Smulson, M. Cancer Res. 54, 4627–4634 (1994).
17. Bürkle, A., Grube, K. and Küpper, J.-H. Exp. Clin. Immunogenet. 9, 230–240 (1992).
18. Kaufmann, S. H., Desnoyers, S., Ottaviano, Y., Davidson, N. E. and Poirier, G. G. Cancer Res. 53, 3976–3985 (1993).
19. Lazebnik, Y. A., Kaufmann, S. H., Desnoyers, S., Poirier, G. G. and Earnshaw, W. C. Nature 371, 346–347 (1994).
20. Yoshihara, K., Tanigawa, Y. and Koide, S. S. Biochem. Biophys. Res. Commun. 59, 658–665 (1974).
21. Yoshihara, K., Tanigawa, Y., Burzio, L. and Koide, S. S. Proc. Natl. Acad. Sci. (U.S.A.) 72, 289–293 (1975).
22. Tanaka, Y., Yoshihara, K., Itaya, A., Kamiya, T. and Koide, S. S. J. Biol. Chem. 259, 6579–6585 (1984).
23. Kumar, S., Kinoshita, M., Noda, M., Copeland, N. G. and Jenkins, N. A. Genes and Develop. 8, 1613–1626 (1994).
24. Wang, L., Miura, M., Bergeron, L., Zhu, J. and Yuan, J. Cell 78, 739–750 (1994).
25. Fernandes-Alnemri, T., Litwack, G. and Alnemri, E. S. J. Biol. Chem. 269, 30761–30764 (1994).
26. Munday, N. A., Vaillancourt, J. P., Ali, A., Casano, F. J., Miller, D. K., Molineaux, S. M., Yamin, T.-T., Yu, V. L. and Nicholson, D. W. J. Biol. Chem. (submitted) (1995)
27. Williams, M. S. and HenKart, P. A. J. Immunol. 153, 4247–54255 (1994).
28. Heusel, J. W., Wesselschmidt, R. L., Shresta, S., Russell, J. H. and Ley, T. J. Cell, 76, 977–987 (1994).
29. Li, P., Allen, H., Banerjee, S., Franklin, S., Herzog, L., Johnston, C., McDowell, J., Paskind, M., Rodman, L., Salfeld, J., Towne, E., Tracey, D., Wardwell, S., Wei, F.-Y., Wong, W., Kamen, R. and Seshadri, T. Cell 80, 401–411 (1995).
30. Ayala, J. M., Yamin, T.-T., Egger, L. A., Chin, L. A., Kostura, M. J. and Miller, D. K. J. Immunol. 153, 2592–2599 (1994).
31. Ray, C. A., Black, R. A., Kronheim, S. R., Greenstreet, T. A., Sleath, P. R., Salvesen, G. S. and Pickup, D. J. Cell 69, 597–604 (1992).
32. Howard, A. D., Palyha, O. C., Griffin, P. R., Peterson, E. P., Lenny, A. B., Ding, G. J.-F., Pickup, D. J., Thornberry, N. A., Schmidt, J. A. and Tocci, M. J. J. Immunol. 154, 2321–2332 (1995).
33. Wilson, K. P., Black, J.-A. F., Thomson, J. A., Kim, E. E., Griffith, J. P., Navia, M. A., Murcko, M. A., Chambers, S. P., Aldape, R. A., Raybuck, S. A. and Livingston, D. J. Nature 370, 270–275 (1994).
34. Walker, N. P. C., Talanian, R. V., Brady, K. D., Dang, L. C., Bump, N. J., Ferenz, C. R., Franklin, S., Ghayur, T., Hackett, M. C., Hammill, L. D., Herzog, L., Hugunin, M., Houy, W., Mankovich, J. A., McGuiness, L., Orlewicz, E., Paskind, M., Pratt, C. A., Reis, P., Summani, A., Terranova, M., Welch, J. P., Xiong, L., Möller, A., Tracey, D. E., Kamen, R. and Wong, W. W. Cell 78, 343–352 (1994).
35. Westerik, J. O. and Wolfenden, R. J. Biol. Chem. 247, 8195–8197 (1972).
36. Lazebnik, Y. A., Cole, S., Cooke, C. A., Nelson, W. G. and Earnshaw, W. C. J. Cell. Biol. 123, 7–22 (1993).
37. deMurcia, G., Ménissier-deMurcia, J. and Schreiber, V. BioEssays 13, 455–462 (1991).
38. Langlois, A. J., Lapis, K., Ishizaki, R., Beard, J. W. and Bolognesi D. P. Cancer Res. 34, 1457–1464 (1974).
39. Cherney, B. W., McBride, O. W., Chen, D., Alkhatib, H., Bhatia, K., Hensley. P. and Smulson, M. E. Proc.Natl.Acad.Sci.(U.S.A.) 84, 8370–8374 (1987).
40. Chapman, K. T. Bioorg. Med. Chem. Lett. 2, 613–618 (1992).
41. Miller, D. K., Ayala, J. M., Egger, L. A., Raju, S. M., Yamin, T.-T., Ding, G. J.-F., Gaffney, E. P., Howard, A. D., Palyha, O. C., Rolando, A. M., Salley, J. P., Thornberry, N. A., Weidner, J. R., Williams, J. H., Chapman, K. T., Jackson, J., Kostura, M. J., Limjuco, G., Molineaux, S. M., Mumford, R. A. and Calaycay, J. R. J. Biol. Chem. 268, 18062–18069 (1993).
42. Devereux, J., Haeberli, P. and Smithies, O. Nucleic Acids Res. 12, 387–395 (1984).
43. Morrison, J. F. Trends Biochem. Sci. 7, 102–105 (1982).

What is claimed is:

1. A compound selected from the group consisting of:
   (a) N-(N-Acetyl-aspartyl-glutamyl-valinyl)-3-amino-3-formylpropionic acid,
   (b) N-(N-(1,1-Dimethylethoxycarbonyl)-aspartyl-glutamyl-valinyl)-3-amino-formylpropionic acid,
   (c) N-(N-(1,1-Dimethylethoxycarbonyl)-aspartyl-glutamyl-valinyl)-3-amino-3-(trifluoromethylcarbonyl)propionic acid,
   (d) N-(N-(N-(1,1-Dimethylethoxycarbonyl)anthranilyl)-aspartyl-glutamyl-valinyl)-3-amino-3-formylpropionic acid,
   (e) N-(N-(3-(2-oxo-hexahydro-thieno[3,4-d]imidazol-4-yl)pentanoyl)-aspartyl-glutamyl-valinyl)-3-amino-3-formylpropionic acid, and
   (f) N-(N-(N-(5-(3a-(S)-6a-(R)-2-oxo-hexahydro-thieno[3,4-d]imidazol-4-yl)pentanoyl)-6-aminohexanoyl)-aspartyl-glutamyl-valinyl)-3-amino-3-formylpropionic acid.

2. A pharmaceutical composition comprising a compound in accordance with claim 1 in combination with a pharmaceutically acceptable carrier.

3. A method of inhibiting pro-apoptotic cysteine proteinase in patient in need of such inhibition, comprising: administering a therapeutically effective non-toxic amount of a compound of formula I, according to claim 1.

* * * * *